(12) United States Patent
Gaspar et al.

(10) Patent No.: US 9,309,309 B2
(45) Date of Patent: Apr. 12, 2016

(54) ANTI-ADDL MONOCLONAL ANTIBODY AND USES THEREOF

(71) Applicant: Merck Sharp & Dohme Corp., Rahway, NJ (US)

(72) Inventors: Renee C. Gaspar, Souderton, PA (US); Paul J. Shughrue, West Chester, PA (US); Fubao Wang, Dresher, PA (US); Weirong Wang, Harleysville, PA (US); Ningyan Zhang, Ambler, PA (US); Wei-Qin Zhao, North Wales, PA (US); Min Xu, Ambler, PA (US); Alexander McCampbell, Chalfont, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/326,974

(22) Filed: Jul. 9, 2014

(65) Prior Publication Data
US 2015/0023952 A1    Jan. 22, 2015

Related U.S. Application Data

(63) Continuation of application No. 13/809,475, filed as application No. PCT/US2011/043866 on Jul. 13, 2011, now abandoned.

(60) Provisional application No. 61/364,210, filed on Jul. 14, 2010.

(51) Int. Cl.
*A61K 39/395* (2006.01)
*C07K 16/18* (2006.01)
*A61K 45/06* (2006.01)
*A61K 39/00* (2006.01)

(52) U.S. Cl.
CPC ............. *C07K 16/18* (2013.01); *A61K 39/3955* (2013.01); *A61K 45/06* (2013.01); *A61K 2039/505* (2013.01); *C07K 2317/24* (2013.01); *C07K 2317/55* (2013.01); *C07K 2317/565* (2013.01); *C07K 2317/64* (2013.01); *C07K 2317/76* (2013.01); *C07K 2317/90* (2013.01); *C07K 2317/92* (2013.01); *C07K 2317/94* (2013.01)

(58) Field of Classification Search
CPC ............... C07K 16/18; C07K 2317/64; C07K 2317/24; C07K 2317/55; C07K 2317/56; C07K 2317/565; A61K 39/3955; A61K 45/06; A61K 2039/505
See application file for complete search history.

(56) References Cited

FOREIGN PATENT DOCUMENTS

WO    WO 2006055178 A2 *  5/2006

* cited by examiner

*Primary Examiner* — Kimberly A. Ballard
(74) *Attorney, Agent, or Firm* — Licata & Tyrrell P.C.

(57) ABSTRACT

The present invention relates to antibodies that bind amyloid β-derived diffusible ligands, also known as ADDLs. The antibodies of the invention are selective for ADDLs, can penetrate the brain, and are useful in methods of detecting ADDLs and diagnosing Alzheimer's disease. The present antibodies also block binding of ADDLs to neurons, assembly of ADDLS, and tau phosphorylation and are there useful in methods for the preventing and treating diseases associated with ADDLs.

10 Claims, 13 Drawing Sheets

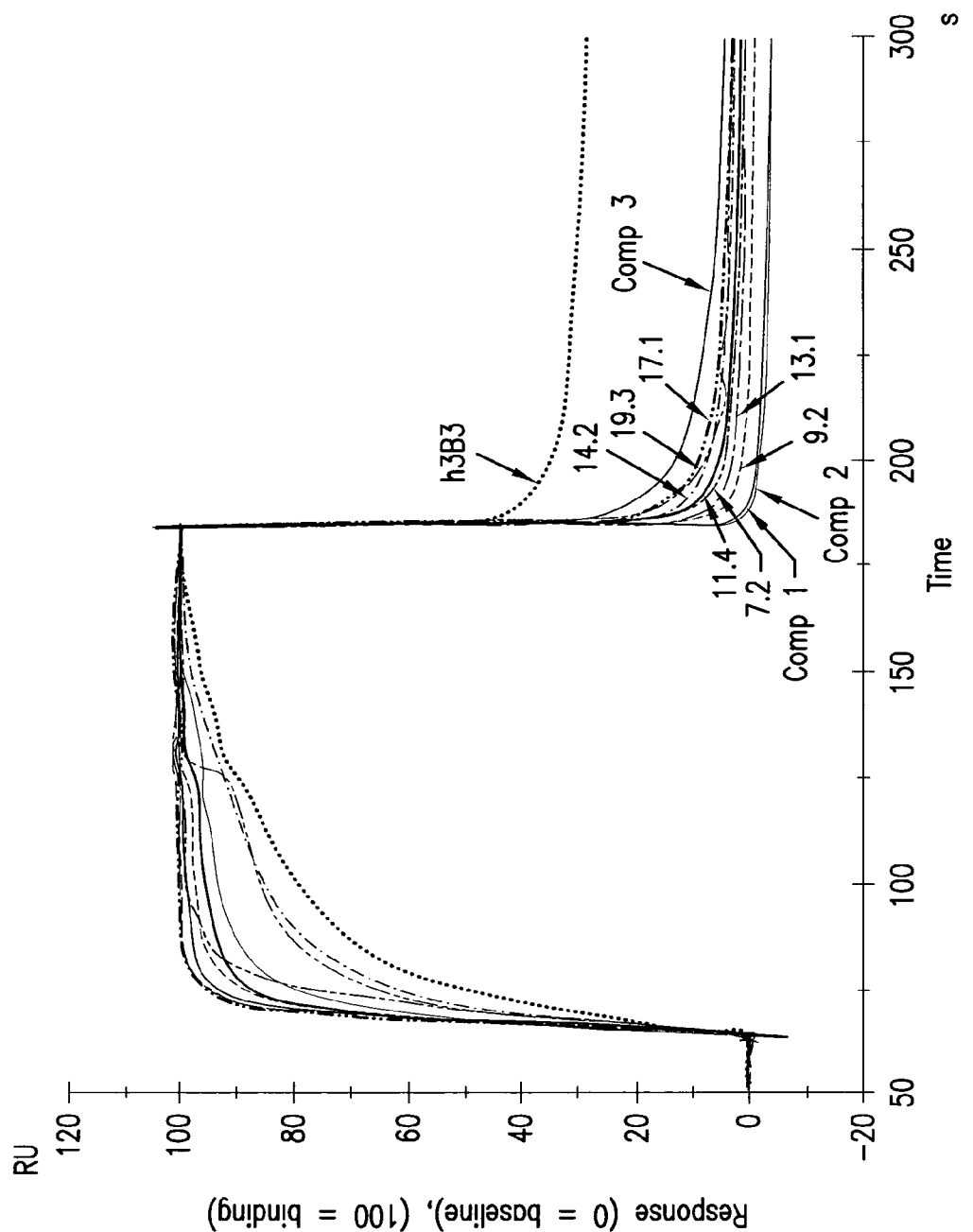

```
19.3_VH          EVQLVESGGGLVQPGGSLRLSCAASGFTFSSFGMHWVRQAPGKGLEWVAYISRGSSTIYY   (SEQ ID NO:17)
HUMAN_VH3-66     EVQLVESGGGLVQPGGSLRLSCAAS---------WVRQAPGKGLEWVS-----------   (SEQ ID NO:69)
                 *************************         **************

19.3_VH          ADTVKGRFTISRDNAKNSLYLQMNSLRAEDTAVYYCARGITTALDYWGQGTLVTVSS
HUMAN_VH3-66     -------RFTISRDNSKNTLYLQMNSLRAEDTAVYYCAR------------------
                        ******** **:*:*****************

19.3_VL          DVVMTQSPLSLPVTPGEPASISCRSSQSIVHSNGNTYLEWYLQKPGQSPQLLIYKASNRF   (SEQ ID NO:70)
HUMAN_VK2-19     DIVMTQSPLSLPVTPGEPASISC--------------------WYLQKPGQSPQLLIY-   (SEQ ID NO:71)
                 *:********************                     ***************

19.3_VL          SGVPDRFSGSGSGTDFTLKISRVEAEDVGVYYCFQGSRLGPSFGQGTKLEIL
HUMAN_VK2-19     -GVPDRFSGSGSGTDFTLKISRVEAEDVGVYYC-------------------
                  ********************************
```

FIG. 6A

```
SEQUENCE LISTING

<160> NUMBER OF SEQ ID NOS: 71

<210> SEQ ID NO 1
<211> LENGTH: 16
<212> TYPE: PRT
<213> ORGANISM: Artificial Sequence
<220> FEATURE:
<223> OTHER INFORMATION: Synthetic

<400> SEQUENCE: 1

Arg Ser Ser Gln Ser Ile Val His Ser Asn Gly Asn Thr Tyr Leu Glu
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: Synthetic

<400> SEQUENCE: 2

Lys Ala Ser Asn Arg Phe Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Xaa denotes Arg, Lys or Tyr
<220> FEATURE:
<221> NAME/KEY: MISC_FEATURE
<222> LOCATION: (6)..(6)
<223> OTHER INFORMATION: Xaa denotes Val, Ala, or Leu
<220> FEATURE:
<221> NAME/KEY: MISC_FEATURE
<222> LOCATION: (7)..(7)
<223> OTHER INFORMATION: Xaa denotes Pro, His, or Gly
<220> FEATURE:
<221> NAME/KEY: misc_feature
```

```
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa denotes Ser, Gly, or Phe

<400> SEQUENCE: 3

Phe Gln Gly Ser Xaa Xaa Xaa Xaa Xaa
1               5

<210> SEQ ID NO 4
<211> LENGTH: 10
<212> TYPE: PRT
<213> ORGANISM: Artificial Sequence
<220> FEATURE:
<223> OTHER INFORMATION: Synthetic

<400> SEQUENCE: 4

Gly Phe Thr Phe Ser Ser Phe Gly Met His
1               5                   10

<210> SEQ ID NO 5
<211> LENGTH: 17
<212> TYPE: PRT
<213> ORGANISM: Artificial Sequence
<220> FEATURE:
<223> OTHER INFORMATION: Synthetic

<400> SEQUENCE: 5

Tyr Ile Ser Arg Gly Ser Ser Thr Ile Tyr Tyr Ala Asp Thr Val Lys
1               5                   10                  15

Gly

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Gly Ile Thr Thr Ala Leu Asp Tyr
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic

<400> SEQUENCE: 7

Phe Gln Gly Ser Arg Val Pro Ala Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic

<400> SEQUENCE: 8

Phe Gln Gly Ser Arg Val Pro Pro Gly
1               5
```

```
<210> SEQ ID NO 9
<211> LENGTH: 9
<212> TYPE: PRT
<213> ORGANISM: Artificial Sequence
<220> FEATURE:
<223> OTHER INFORMATION: Synthetic

<400> SEQUENCE: 9

Phe Gln Gly Ser Lys Ala His Pro Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic

<400> SEQUENCE: 10

Phe Gln Gly Ser Arg Leu Gly Pro Ser
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic

<400> SEQUENCE: 11

Phe Gln Gly Ser Tyr Ala Pro Pro Gly
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic

<400> SEQUENCE: 12

Phe Gln Gly Ser Arg Ala Pro Pro Phe
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic

<400> SEQUENCE: 13

Phe Gln Gly Ser Arg Val Pro Val Arg
1               5

<210> SEQ ID NO 14
<211> LENGTH: 354
<212> TYPE: DNA
<213> ORGANISM: Artificial Sequence
<220> FEATURE:
<223> OTHER INFORMATION: Synthetic

<400> SEQUENCE: 14
gcttctagag atgtggtgat gacccagagc cccctgtccc tgcctgtgac ccctggcgag      60
cctgccagca tctcctgccg gagctcccag agcatcgtgc actccaatgg caacacctac     120
```

```
ctggagtggt acctgcagaa gcctggccag agcccccagc tgctgatcta caaggcttcc    180
aaccggttct ccggcgtgcc tgaccggttc agcggctccg gcagcggcac agacttcacc    240
ctgaagatca gccgggtgga ggctgaggat gtgggcgtct actactgctt ccagggcagc    300
cggcttggtc ctagttttgg ccagggcacc aagctggaga tcaagcgtac ggtg          354
```

<210> SEQ ID NO 15
<211> LENGTH: 115
<212> TYPE: PRT
<213> ORGANISM: Artificial Sequence
<220> FEATURE:
<223> OTHER INFORMATION: Synthetic

<400> SEQUENCE: 15

```
Ala Ser Arg Asp Val Val Met Thr Gln Ser Pro Leu Ser Leu Pro Val
1               5                   10                  15

Thr Pro Gly Glu Pro Ala Ser Ile Ser Cys Arg Ser Ser Gln Ser Ile
            20                  25                  30

Val His Ser Asn Gly Asn Thr Tyr Leu Glu Trp Tyr Leu Gln Lys Pro
        35                  40                  45

Gly Gln Ser Pro Gln Leu Leu Ile Tyr Lys Ala Ser Asn Arg Phe Ser
    50                  55                  60

Gly Val Pro Asp Arg Phe Ser Gly Ser Gly Ser Gly Thr Asp Phe Thr
65                  70                  75                  80

Leu Lys Ile Ser Arg Val Glu Ala Glu Asp Val Gly Val Tyr Tyr Cys
                85                  90                  95

Phe Gln Gly Ser Arg Leu Gly Pro Ser Phe Gly Gln Gly Thr Lys Leu
            100                 105                 110

Glu Ile Lys
        115
```

<210> SEQ ID NO 16
<211> LENGTH: 351
<212> TYPE: DNA
<213> ORGANISM: Artificial Sequence
<220> FEATURE:
<223> OTHER INFORMATION: Synthetic

<400> SEQUENCE: 16

```
gaggtgcagc tggtggagtc cggcggcggc ctggtgcagc ctggcggcag cctgcggctg    60
agctgtgctg cctctggctt caccttcagc tcctttggca tgcactgggt gcggcaggcc    120
cctggcaagg gcctggagtg gtggccctac atcagccggg gctccagcac catctactat    180
gctgacacag tgaagggccg gttcaccatc agccgggaca tgccaagaa ctccctgtat     240
ctgcagatga acagcctgcg ggctgaggac acagcagtgt actactgtgc ccggggcatc    300
accacagccc tggactactg gggccagggc accctggtga ccgtgtccag c             351
```

<210> SEQ ID NO 17
<211> LENGTH: 117
<212> TYPE: PRT
<213> ORGANISM: Artificial Sequence
<220> FEATURE:
<223> OTHER INFORMATION: Synthetic

<400> SEQUENCE: 17

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30
```

Gly Met His Trp Val Arg Gln Ala Pro Gly Lys Gly Leu Glu Trp Val
            35                  40                  45

Ala Tyr Ile Ser Arg Gly Ser Ser Thr Ile Tyr Tyr Ala Asp Thr Val
        50                  55                  60

Lys Gly Arg Phe Thr Ile Ser Arg Asp Asn Ala Lys Asn Ser Leu Tyr
 65                 70                  75                  80

Leu Gln Met Asn Ser Leu Arg Ala Glu Asp Thr Ala Val Tyr Tyr Cys
                85                  90                  95

Ala Arg Gly Ile Thr Thr Ala Leu Asp Tyr Trp Gly Gln Gly Thr Leu
            100                 105                 110

Val Thr Val Ser Ser
            115

<210> SEQ ID NO 18
<211> LENGTH: 324
<212> TYPE: DNA
<213> ORGANISM: Artificial Sequence
<220> FEATURE:
<223> OTHER INFORMATION: Synthetic

<400> SEQUENCE: 18
cgtacggtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct caatcgggt aactcccagg agagtgtcac agagcaggac      180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg ttag                                            324

<210> SEQ ID NO 19
<211> LENGTH: 107
<212> TYPE: PRT
<213> ORGANISM: Artificial Sequence
<220> FEATURE:
<223> OTHER INFORMATION: Synthetic

<400> SEQUENCE: 19

Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
 65                 70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 20
<211> LENGTH: 981
<212> TYPE: DNA
<213> ORGANISM: Artificial Sequence
<220> FEATURE:
<223> OTHER INFORMATION: Synthetic

<400> SEQUENCE: 20

```
gcatccacca agggcccatc cgtcttcccc ctggcgccct gctccaggag cacctccgag        60
agcacagccg ccctgggctg cctggtcaag gactacttcc ccgaaccggt gacggtgtcc       120
tggaactctg gcgccctgac ctctggcgtg cacaccttcc ctgctgtgct gcaatcctct       180
ggcctgtact ccctgtcctc tgtggtgaca gtgccatcct ccaacttcgg cacccagacc       240
tacacatgca atgtggacca caagccatcc aacaccaagg tggacaagac agtggagcgg       300
aagtgctgtg tggagtgccc cccatgccct gcccccctg tggctggccc atctgtgttc        360
ctgttccccc ccaagcccaa ggacaccctg atgatctccc ggacccctga ggtgacctgt       420
gtggtggtgg acgtgtccca tgaggaccct gaggtgcagt tcaactggta tgtggatggc       480
gtggaggtgc acaatgccaa gaccaagccc cgggaggagc agttcaactc caccttccgg       540
gtggtgtctg tgctgacagt ggtgcaccag gactggctga atggcaagga gtacaagtgc       600
aaggtgtcca acaagggcct gcctgccccc atcgagaaga ccatctccaa gaccaagggc       660
cagccccggg agccccaggt gtacaccctg cccccatccc gggaggagat gaccaagaac       720
caggtgtccc tgacctgcct ggtgaagggc ttctacccat ccgacattgc tgtggagtgg       780
gagtccaatg ccagcctga gaacaactac aagaccaccc cccccatgct ggactctgat       840
ggctccttct cctgtactc caagctgaca gtggacaagt cccggtggca gcagggcaat       900
gtgttctcct gctctgtgat gcatgaggcc ctgcacaacc actacaccca gaagtccctg       960
tccctgtccc ctggcaagtg a                                                 981
```

<210> SEQ ID NO 21
<211> LENGTH: 326
<212> TYPE: PRT
<213> ORGANISM: Artificial Sequence
<220> FEATURE:
<223> OTHER INFORMATION: Synthetic

<400> SEQUENCE: 21

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175
```

```
Ser Thr Phe Arg Val Val Ser Val Leu Thr Val Val His Gln Asp Trp
            180                 185                 190
Leu Asn Gly Lys Glu Tyr Lys Cys Lys Val Ser Asn Lys Gly Leu Pro
        195                 200                 205
Ala Pro Ile Glu Lys Thr Ile Ser Lys Thr Lys Gly Gln Pro Arg Glu
    210                 215                 220
Pro Gln Val Tyr Thr Leu Pro Pro Ser Arg Glu Glu Met Thr Lys Asn
225                 230                 235                 240
Gln Val Ser Leu Thr Cys Leu Val Lys Gly Phe Tyr Pro Ser Asp Ile
            245                 250                 255
Ala Val Glu Trp Glu Ser Asn Gly Gln Pro Glu Asn Asn Tyr Lys Thr
        260                 265                 270
Thr Pro Pro Met Leu Asp Ser Asp Gly Ser Phe Phe Leu Tyr Ser Lys
    275                 280                 285
Leu Thr Val Asp Lys Ser Arg Trp Gln Gln Gly Asn Val Phe Ser Cys
290                 295                 300
Ser Val Met His Glu Ala Leu His Asn His Tyr Thr Gln Lys Ser Leu
305                 310                 315                 320
Ser Leu Ser Pro Gly Lys
            325

<210> SEQ ID NO 22
<211> LENGTH: 25
<212> TYPE: DNA
<213> ORGANISM: Artificial Sequence
<220> FEATURE:
<223> OTHER INFORMATION: Synthetic

<400> SEQUENCE: 22
tatggcttct agagatgtgg tgatg                                        25

<210> SEQ ID NO 23
<211> LENGTH: 82
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (62)..(63)
<223> OTHER INFORMATION: n is a, c, g, or t
<220> FEATURE:
<221> NAME/KEY: misc_feature
<222> LOCATION: (65)..(66)
<223> OTHER INFORMATION: n is a, c, g, or t
<220> FEATURE:
<221> NAME/KEY: misc_feature
<222> LOCATION: (68)..(69)
<223> OTHER INFORMATION: n is a, c, g, or t
<220> FEATURE:
<221> NAME/KEY: misc_feature
<222> LOCATION: (71)..(72)
<223> OTHER INFORMATION: n is a, c, g, or t

<400> SEQUENCE: 23
tgcagccacc gtacgcttga tctccagctt ggtgccctgg ccaaaggtgg ggggcacmnn    60
mnnmnnmnnm nngcagtagt ag                                            82

<210> SEQ ID NO 24
```

```
<211> LENGTH: 70
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t

<400> SEQUENCE: 24
tgcagccacc gtacgcttga tctccagctt ggtgccctgg ccaaamnnmn nmnnmnnmnn      60
gctgccctgg                                                             70

<210> SEQ ID NO 25
<211> LENGTH: 24
<212> TYPE: DNA
<213> ORGANISM: Artificial Sequence
<220> FEATURE:
<223> OTHER INFORMATION: Synthetic

<400> SEQUENCE: 25
aggcggccct cgaggaggtg cagc                                             24

<210> SEQ ID NO 26
<211> LENGTH: 83
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (60)..(61)
<223> OTHER INFORMATION: n is a, c, g, or t
<220> FEATURE:
<221> NAME/KEY: misc_feature
<222> LOCATION: (63)..(64)
<223> OTHER INFORMATION: n is a, c, g, or t
<220> FEATURE:
<221> NAME/KEY: misc_feature
<222> LOCATION: (66)..(67)
<223> OTHER INFORMATION: n is a, c, g, or t
<220> FEATURE:
<221> NAME/KEY: misc_feature
<222> LOCATION: (69)..(70)
<223> OTHER INFORMATION: n is a, c, g, or t
<220> FEATURE:
<221> NAME/KEY: misc_feature
<222> LOCATION: (72)..(73)
<223> OTHER INFORMATION: n is a, c, g, or t

<400> SEQUENCE: 26
agaccgatgg gcccttggtg gaggcgctgg acacggtcac cagggtgccc tggccccamn      60
nmnnmnnmnn mnnggtgatg ccc                                              83
```

```
<210> SEQ ID NO 27
<211> LENGTH: 92
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (69)..(70)
<223> OTHER INFORMATION: n is a, c, g, or t
<220> FEATURE:
<221> NAME/KEY: misc_feature
<222> LOCATION: (72)..(73)
<223> OTHER INFORMATION: n is a, c, g, or t
<220> FEATURE:
<221> NAME/KEY: misc_feature
<222> LOCATION: (75)..(76)
<223> OTHER INFORMATION: n is a, c, g, or t
<220> FEATURE:
<221> NAME/KEY: misc_feature
<222> LOCATION: (78)..(79)
<223> OTHER INFORMATION: n is a, c, g, or t
<220> FEATURE:
<221> NAME/KEY: misc_feature
<222> LOCATION: (81)..(82)
<223> OTHER INFORMATION: n is a, c, g, or t

<400> SEQUENCE: 27
agaccgatgg gcccttggtg gaggcgctgg acacggtcac cagggtgccc tggccccagt    60
agtccagmnn mnnmnnmnnm nnccgggcac ag                                  92

<210> SEQ ID NO 28
<211> LENGTH: 9
<212> TYPE: PRT
<213> ORGANISM: Artificial Sequence
<220> FEATURE:
<223> OTHER INFORMATION: Synthetic

<400> SEQUENCE: 28

Phe Gln Gly Ser His Val Pro Pro Thr
1               5

<210> SEQ ID NO 29
<211> LENGTH: 57
<212> TYPE: DNA
<213> ORGANISM: Artificial Sequence
<220> FEATURE:
<223> OTHER INFORMATION: Synthetic

<400> SEQUENCE: 29
atggaatgga gctgggtctt tctcttcttc ctgtcagtaa ctacaggtgt ccactcg       57

<210> SEQ ID NO 30
<211> LENGTH: 16
<212> TYPE: PRT
<213> ORGANISM: Artificial Sequence
<220> FEATURE:
<223> OTHER INFORMATION: Synthetic

<400> SEQUENCE: 30

Met Glu Trp Ser Trp Val Phe Leu Phe Phe Leu Ser Val Thr Thr Gly
1               5                   10                  15

<210> SEQ ID NO 31
<211> LENGTH: 60
<212> TYPE: DNA
<213> ORGANISM: Artificial Sequence
<220> FEATURE:
<223> OTHER INFORMATION: Synthetic
```

<400> SEQUENCE: 31
atgagtgtgc ccactcaggt cctggggttg ctgctgctgt ggcttacaga tgccagatgc    60

<210> SEQ ID NO 32
<211> LENGTH: 20
<212> TYPE: PRT
<213> ORGANISM: Artificial Sequence
<220> FEATURE:
<223> OTHER INFORMATION: Synthetic

<400> SEQUENCE: 32

Met Ser Val Pro Thr Gln Val Leu Gly Leu Leu Leu Trp Leu Thr
1               5                   10                  15

Asp Ala Arg Cys
            20

<210> SEQ ID NO 33
<211> LENGTH: 95
<212> TYPE: PRT
<213> ORGANISM: Artificial Sequence
<220> FEATURE:
<223> OTHER INFORMATION: Synthetic

<400> SEQUENCE: 33

Pro Ala Ser Ile Ser Cys Arg Ser Ser Gln Ser Ile Val His Ser Asn
1               5                   10                  15

Gly Asn Thr Tyr Leu Glu Trp Tyr Leu Gln Lys Pro Gly Gln Ser Pro
            20                  25                  30

Gln Leu Leu Ile Tyr Lys Ala Ser Asn Arg Phe Ser Gly Val Pro Asp
        35                  40                  45

Arg Phe Ser Gly Ser Gly Ser Gly Thr Asp Phe Thr Leu Lys Ile Ser
    50                  55                  60

Arg Val Glu Ala Glu Asp Val Gly Val Tyr Tyr Cys Phe Gln Gly Ser
65                  70                  75                  80

Arg Val Pro Ala Ser Phe Gly Gln Gly Thr Lys Leu Glu Ile Lys
                85                  90                  95

<210> SEQ ID NO 34
<211> LENGTH: 95
<212> TYPE: PRT
<213> ORGANISM: Artificial Sequence
<220> FEATURE:
<223> OTHER INFORMATION: Synthetic

<400> SEQUENCE: 34

Pro Ala Ser Ile Ser Cys Arg Ser Ser Gln Ser Ile Val His Ser Asn
1               5                   10                  15

Gly Asn Thr Tyr Leu Glu Trp Tyr Leu Gln Lys Pro Gly Gln Ser Pro
            20                  25                  30

Gln Leu Leu Ile Tyr Lys Ala Ser Asn Arg Phe Ser Gly Val Pro Asp
        35                  40                  45

Arg Phe Ser Gly Ser Gly Ser Gly Thr Asp Phe Thr Leu Lys Ile Ser
    50                  55                  60

Arg Val Glu Ala Glu Asp Val Gly Val Tyr Tyr Cys Phe Gln Gly Ser
65                  70                  75                  80

Arg Val Pro Pro Gly Phe Gly Gln Gly Thr Lys Leu Glu Ile Lys
                85                  90                  95

<210> SEQ ID NO 35
<211> LENGTH: 95

```
<212> TYPE: PRT
<213> ORGANISM: Artificial Sequence
<220> FEATURE:
<223> OTHER INFORMATION: Synthetic

<400> SEQUENCE: 35

Pro Ala Ser Ile Ser Cys Arg Ser Ser Gln Ser Ile Val His Ser Asn
1               5                   10                  15

Gly Asn Thr Tyr Leu Glu Trp Tyr Leu Gln Lys Pro Gly Gln Ser Pro
            20                  25                  30

Gln Leu Leu Ile Tyr Lys Ala Ser Asn Arg Phe Ser Gly Val Pro Asp
        35                  40                  45

Arg Phe Ser Gly Ser Gly Ser Gly Thr Asp Phe Ile Leu Lys Ile Ser
    50                  55                  60

Arg Val Glu Ala Glu Asp Val Gly Val Tyr Tyr Cys Phe Gln Gly Ser
65                  70                  75                  80

Lys Ala His Pro Ser Phe Gly Gln Gly Thr Lys Leu Glu Ile Lys
                85                  90                  95

<210> SEQ ID NO 36
<211> LENGTH: 95
<212> TYPE: PRT
<213> ORGANISM: Artificial Sequence
<220> FEATURE:
<223> OTHER INFORMATION: Synthetic

<400> SEQUENCE: 36

Pro Ala Ser Ile Ser Cys Arg Ser Ser Gln Ser Ile Val His Ser Asn
1               5                   10                  15

Gly Asn Thr Tyr Leu Glu Trp Tyr Leu Gln Lys Pro Gly Gln Ser Pro
            20                  25                  30

Gln Leu Leu Ile Tyr Lys Ala Ser Asn Arg Phe Ser Gly Val Pro Asp
        35                  40                  45

Arg Phe Ser Gly Ser Gly Ser Gly Thr Asp Phe Thr Leu Lys Ile Ser
    50                  55                  60

Arg Val Glu Ala Glu Asp Val Gly Val Tyr Tyr Cys Phe Gln Gly Ser
65                  70                  75                  80

Arg Leu Gly Pro Ser Phe Gly Gln Gly Thr Lys Leu Glu Ile Lys
                85                  90                  95

<210> SEQ ID NO 37
<211> LENGTH: 95
<212> TYPE: PRT
<213> ORGANISM: Artificial Sequence
<220> FEATURE:
<223> OTHER INFORMATION: Synthetic

<400> SEQUENCE: 37

Pro Ala Ser Ile Ser Cys Arg Ser Ser Gln Ser Ile Val His Ser Asn
1               5                   10                  15

Gly Asn Thr Tyr Leu Glu Trp Tyr Leu Gln Lys Pro Gly Gln Ser Pro
            20                  25                  30

Gln Leu Leu Ile Tyr Lys Ala Ser Asn Arg Phe Ser Gly Val Pro Asp
        35                  40                  45

Arg Phe Ser Gly Ser Gly Ser Gly Thr Asp Phe Thr Leu Lys Ile Ser
    50                  55                  60

Arg Val Glu Ala Glu Asp Val Gly Val Tyr Tyr Cys Phe Gln Gly Ser
65                  70                  75                  80

Tyr Ala Pro Pro Gly Phe Gly Gln Gly Thr Lys Leu Glu Ile Lys
```

<210> SEQ ID NO 38
<211> LENGTH: 95
<212> TYPE: PRT
<213> ORGANISM: Artificial Sequence
<220> FEATURE:
<223> OTHER INFORMATION: Synthetic

<400> SEQUENCE: 38

Pro Ala Ser Ile Ser Cys Arg Ser Ser Gln Ser Ile Val His Ser Asn
1               5                   10                  15

Gly Asn Thr Tyr Leu Glu Trp Tyr Leu Gln Lys Pro Gly Gln Ser Pro
            20                  25                  30

Gln Leu Leu Ile Tyr Lys Ala Ser Asn Arg Phe Ser Gly Val Pro Asp
        35                  40                  45

Arg Phe Ser Gly Ser Gly Ser Gly Thr Asp Phe Thr Leu Lys Ile Ser
    50                  55                  60

Arg Val Glu Ala Glu Asp Val Gly Val Tyr Tyr Cys Phe Gln Gly Ser
65                  70                  75                  80

Arg Ala Pro Pro Phe Phe Gly Gln Gly Thr Lys Leu Glu Ile Lys
                85                  90                  95

<210> SEQ ID NO 39
<211> LENGTH: 95
<212> TYPE: PRT
<213> ORGANISM: Artificial Sequence
<220> FEATURE:
<223> OTHER INFORMATION: Synthetic

<400> SEQUENCE: 39

Pro Ala Ser Ile Ser Cys Arg Ser Ser Gln Ser Ile Val His Ser Asn
1               5                   10                  15

Gly Asn Thr Tyr Leu Glu Trp Tyr Leu Gln Lys Pro Gly Gln Ser Pro
            20                  25                  30

Gln Leu Leu Ile Tyr Lys Ala Ser Asn Arg Phe Ser Gly Val Pro Asp
        35                  40                  45

Arg Phe Ser Gly Ser Gly Ser Gly Thr Asp Phe Thr Leu Lys Ile Ser
    50                  55                  60

Arg Val Glu Ala Glu Asp Val Gly Val Tyr Tyr Cys Phe Gln Gly Ser
65                  70                  75                  80

Arg Val Pro Val Arg Phe Gly Gln Gly Thr Lys Leu Glu Ile Lys
                85                  90                  95

<210> SEQ ID NO 40
<211> LENGTH: 95
<212> TYPE: PRT
<213> ORGANISM: Artificial Sequence
<220> FEATURE:
<223> OTHER INFORMATION: Synthetic

<400> SEQUENCE: 40

Pro Ala Ser Ile Ser Cys Arg Ser Ser Gln Ser Ile Val His Ser Asn
1               5                   10                  15

Gly Asn Thr Tyr Leu Glu Trp Tyr Leu Gln Lys Pro Gly Gln Ser Pro
            20                  25                  30

Gln Leu Leu Ile Tyr Lys Ala Ser Asn Arg Phe Ser Gly Val Pro Asp
        35                  40                  45

Arg Phe Ser Gly Ser Gly Ser Gly Thr Asp Phe Thr Leu Lys Ile Ser
    50                  55                  60

```
Arg Val Glu Ala Glu Asp Val Gly Val Tyr Tyr Cys Phe Gln Gly Ser
 65                  70                  75                  80

His Val Pro Pro Thr Phe Gly Gln Gly Thr Lys Leu Glu Ile Lys
                 85                  90                  95

<210> SEQ ID NO 41
<211> LENGTH: 219
<212> TYPE: PRT
<213> ORGANISM: Artificial Sequence
<220> FEATURE:
<223> OTHER INFORMATION: Synthetic

<400> SEQUENCE: 41

Asp Val Val Met Thr Gln Ser Pro Leu Ser Leu Pro Val Thr Pro Gly
  1               5                  10                  15

Glu Pro Ala Ser Ile Ser Cys Arg Ser Ser Gln Ser Ile Val His Ser
                 20                  25                  30

Asn Gly Asn Thr Tyr Leu Glu Trp Tyr Leu Gln Lys Pro Gly Gln Ser
             35                  40                  45

Pro Gln Leu Leu Ile Tyr Lys Ala Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser Arg Leu Gly Pro Ser Phe Gly Gln Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 42
<211> LENGTH: 443
<212> TYPE: PRT
<213> ORGANISM: Artificial Sequence
<220> FEATURE:
<223> OTHER INFORMATION: Synthetic

<400> SEQUENCE: 42

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Phe
                 20                  25                  30

Gly Met His Trp Val Arg Gln Ala Pro Gly Lys Gly Leu Glu Trp Val
             35                  40                  45

Ala Tyr Ile Ser Arg Gly Ser Ser Thr Ile Tyr Tyr Ala Asp Thr Val
```

```
            50                  55                  60
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Ile Thr Thr Ala Leu Asp Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
            195                 200                 205

Thr Lys Val Asp Lys Thr Val Glu Arg Lys Cys Cys Val Glu Cys Pro
210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
            275                 280                 285

Glu Glu Gln Phe Asn Ser Thr Phe Arg Val Val Ser Val Leu Thr Val
290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
            370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
            435                 440

<210> SEQ ID NO 43
<211> LENGTH: 330
<212> TYPE: PRT
<213> ORGANISM: Artificial Sequence
```

<220> FEATURE:
<223> OTHER INFORMATION: Synthetic

<400> SEQUENCE: 43

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 44
<211> LENGTH: 326
<212> TYPE: PRT
<213> ORGANISM: Artificial Sequence
<220> FEATURE:
<223> OTHER INFORMATION: Synthetic

<400> SEQUENCE: 44

Ala Ser Thr Lys Gly Pro Ser Val Phe Pro Leu Ala Pro Cys Ser Arg

```
  1               5                  10                 15
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 45
<211> LENGTH: 327
<212> TYPE: PRT
<213> ORGANISM: Artificial Sequence
<220> FEATURE:
<223> OTHER INFORMATION: Synthetic

<400> SEQUENCE: 45

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
```

```
                 35                  40                  45
Gly Val His Thr Phe Pro Ala Val Leu Gln Ser Ser Gly Leu Tyr Ser
             50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 46
<211> LENGTH: 326
<212> TYPE: PRT
<213> ORGANISM: Artificial Sequence
<220> FEATURE:
<223> OTHER INFORMATION: Synthetic

<400> SEQUENCE: 46

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Thr Ser Ser Asn Phe Gly Thr Gln Thr
```

```
            65                  70                  75                  80

Tyr Thr Cys Asn Val Asp His Lys Pro Ser Asn Thr Lys Val Asp Lys
                        85                  90                  95

Thr Val Glu Arg Lys Cys Cys Val Glu Cys Pro Cys Pro Ala Pro
                    100                 105                 110

Pro Val Ala Gly Pro Ser Val Phe Leu Phe Pro Pro Lys Pro Lys Asp
                        115                 120                 125

Thr Leu Met Ile Ser Arg Thr Pro Glu Val Thr Cys Val Val Asp
                    130                 135                 140

Val Ser Gln Glu Asp Pro Glu Val Gln Phe Asn Trp Tyr Val Asp Gly
        145                 150                 155                 160

Val Glu Val His Asn Ala Lys Thr Lys Pro Arg Glu Glu Gln Phe Asn
                        165                 170                 175

Ser Thr Phe Arg Val Val Ser Val Leu Thr Val Leu His Gln Asp Trp
                    180                 185                 190

Leu Asn Gly Lys Glu Tyr Lys Cys Lys Val Ser Asn Lys Gly Leu Pro
                    195                 200                 205

Ser Ser Ile Glu Lys Thr Ile Ser Lys Thr Lys Gly Gln Pro Arg Glu
                    210                 215                 220

Pro Gln Val Tyr Thr Leu Pro Pro Ser Arg Glu Glu Met Thr Lys Asn
        225                 230                 235                 240

Gln Val Ser Leu Thr Cys Leu Val Lys Gly Phe Tyr Pro Ser Asp Ile
                        245                 250                 255

Ala Val Glu Trp Glu Ser Asn Gly Gln Pro Glu Asn Asn Tyr Lys Thr
                    260                 265                 270

Thr Pro Pro Met Leu Asp Ser Asp Gly Ser Phe Phe Leu Tyr Ser Lys
                    275                 280                 285

Leu Thr Val Asp Lys Ser Arg Trp Gln Gln Gly Asn Val Phe Ser Cys
                    290                 295                 300

Ser Val Met His Glu Ala Leu His Asn His Tyr Thr Gln Lys Ser Leu
        305                 310                 315                 320

Ser Leu Ser Pro Gly Lys
                        325

<210> SEQ ID NO 47
<211> LENGTH: 25
<212> TYPE: PRT
<213> ORGANISM: Artificial Sequence
<220> FEATURE:
<223> OTHER INFORMATION: Synthetic

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 48
<211> LENGTH: 14
<212> TYPE: PRT
<213> ORGANISM: Artificial Sequence
<220> FEATURE:
<223> OTHER INFORMATION: Synthetic

<400> SEQUENCE: 48

Trp Val Arg Gln Ala Pro Gly Lys Gly Leu Glu Trp Val Ser
1               5                   10
```

<210> SEQ ID NO 49
<211> LENGTH: 32
<212> TYPE: PRT
<213> ORGANISM: Artificial Sequence
<220> FEATURE:
<223> OTHER INFORMATION: Synthetic

<400> SEQUENCE: 49

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 50
<211> LENGTH: 23
<212> TYPE: PRT
<213> ORGANISM: Artificial Sequence
<220> FEATURE:
<223> OTHER INFORMATION: Synthetic

<400> SEQUENCE: 50

Asp Ile Val Met Thr Gln Ser Pro Leu Ser Leu Pro Val Thr Pro Gly
1               5                   10                  15

Glu Pro Ala Ser Ile Ser Cys
            20

<210> SEQ ID NO 51
<211> LENGTH: 15
<212> TYPE: PRT
<213> ORGANISM: Artificial Sequence
<220> FEATURE:
<223> OTHER INFORMATION: Synthetic

<400> SEQUENCE: 51

Trp Tyr Leu Gln Lys Pro Gly Gln Ser Pro Gln Leu Leu Ile Tyr
1               5                   10                  15

<210> SEQ ID NO 52
<211> LENGTH: 32
<212> TYPE: PRT
<213> ORGANISM: Artificial Sequence
<220> FEATURE:
<223> OTHER INFORMATION: Synthetic

<400> SEQUENCE: 52

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 53
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: Xaa denotes Asn or Ser
<220> FEATURE:
<221> NAME/KEY: MISC_FEATURE
<222> LOCATION: (12)..(12)
<223> OTHER INFORMATION: Xaa denotes Asn, Gln, Asp, Ser, His or Ala

<400> SEQUENCE: 53

Arg Ser Ser Gln Ser Ile Val His Ser Xaa Gly Xaa Thr Tyr Leu Glu
1               5                   10                  15

<210> SEQ ID NO 54
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa denotes Asn, Gln, Ala or Ser

<400> SEQUENCE: 54

Lys Ala Ser Xaa Arg Phe Ser
1               5

<210> SEQ ID NO 55
<211> LENGTH: 16
<212> TYPE: PRT
<213> ORGANISM: Artificial Sequence
<220> FEATURE:
<223> OTHER INFORMATION: Synthetic

<400> SEQUENCE: 55

Arg Ser Ser Gln Ser Ile Val His Ser Gly Asn Thr Tyr Leu Glu
1               5                   10                  15

<210> SEQ ID NO 56
<211> LENGTH: 16
<212> TYPE: PRT
<213> ORGANISM: Artificial Sequence
<220> FEATURE:
<223> OTHER INFORMATION: Synthetic

<400> SEQUENCE: 56

Arg Ser Ser Gln Ser Ile Val His Ser Thr Gly Asn Thr Tyr Leu Glu
1               5                   10                  15

<210> SEQ ID NO 57
<211> LENGTH: 16
<212> TYPE: PRT
<213> ORGANISM: Artificial Sequence
<220> FEATURE:
<223> OTHER INFORMATION: Synthetic

<400> SEQUENCE: 57

Arg Ser Ser Gln Ser Ile Val His Ser Ala Gly Asn Thr Tyr Leu Glu
1               5                   10                  15

<210> SEQ ID NO 58
<211> LENGTH: 16
<212> TYPE: PRT
<213> ORGANISM: Artificial Sequence
<220> FEATURE:
<223> OTHER INFORMATION: Synthetic

<400> SEQUENCE: 58

Arg Ser Ser Gln Ser Ile Val His Ser Ser Gly His Thr Tyr Leu Glu
1               5                   10                  15

<210> SEQ ID NO 59
<211> LENGTH: 16
<212> TYPE: PRT
<213> ORGANISM: Artificial Sequence
<220> FEATURE:
<223> OTHER INFORMATION: Synthetic

<400> SEQUENCE: 59

Arg Ser Ser Gln Ser Ile Val His Ser Ser Gly Gln Thr Tyr Leu Glu
1               5                   10                  15

<210> SEQ ID NO 60
<211> LENGTH: 16
<212> TYPE: PRT
<213> ORGANISM: Artificial Sequence
<220> FEATURE:
<223> OTHER INFORMATION: Synthetic

<400> SEQUENCE: 60

Arg Ser Ser Gln Ser Ile Val His Ser Ser Gly Ser Thr Tyr Leu Glu
1               5                   10                  15

<210> SEQ ID NO 61
<211> LENGTH: 16
<212> TYPE: PRT
<213> ORGANISM: Artificial Sequence
<220> FEATURE:
<223> OTHER INFORMATION: Synthetic

<400> SEQUENCE: 61

Arg Ser Ser Gln Ser Ile Val His Ser Ser Gly Thr Thr Tyr Leu Glu
1               5                   10                  15

<210> SEQ ID NO 62
<211> LENGTH: 16
<212> TYPE: PRT
<213> ORGANISM: Artificial Sequence
<220> FEATURE:
<223> OTHER INFORMATION: Synthetic

<400> SEQUENCE: 62

Arg Ser Ser Gln Ser Ile Val His Ser Ser Gly Ala Thr Tyr Leu Glu
1               5                   10                  15

<210> SEQ ID NO 63
<211> LENGTH: 7
<212> TYPE: PRT
<213> ORGANISM: Artificial Sequence
<220> FEATURE:
<223> OTHER INFORMATION: Synthetic

<400> SEQUENCE: 63

Lys Ala Ser Gln Arg Phe Ser
1               5

<210> SEQ ID NO 64
<211> LENGTH: 7
<212> TYPE: PRT
<213> ORGANISM: Artificial Sequence
<220> FEATURE:
<223> OTHER INFORMATION: Synthetic

<400> SEQUENCE: 64

Lys Ala Ser Ser Arg Phe Ser
1               5

<210> SEQ ID NO 65
<211> LENGTH: 7
<212> TYPE: PRT
<213> ORGANISM: Artificial Sequence
<220> FEATURE:
<223> OTHER INFORMATION: Synthetic

```
<400> SEQUENCE: 65

Lys Ala Ser Thr Arg Phe Ser
1               5

<210> SEQ ID NO 66
<211> LENGTH: 7
<212> TYPE: PRT
<213> ORGANISM: Artificial Sequence
<220> FEATURE:
<223> OTHER INFORMATION: Synthetic

<400> SEQUENCE: 66

Lys Ala Ser Ala Arg Phe Ser
1               5

<210> SEQ ID NO 67
<211> LENGTH: 16
<212> TYPE: PRT
<213> ORGANISM: Artificial Sequence
<220> FEATURE:
<223> OTHER INFORMATION: Synthetic

<400> SEQUENCE: 67

Arg Ser Ser Gln Ser Ile Val His Ser Glu Gly Asn Thr Tyr Leu Glu
1               5                   10                  15

<210> SEQ ID NO 68
<211> LENGTH: 16
<212> TYPE: PRT
<213> ORGANISM: Artificial Sequence
<220> FEATURE:
<223> OTHER INFORMATION: Synthetic

<400> SEQUENCE: 68

Arg Ser Ser Gln Ser Ile Val His Ser Asp Gly Asn Thr Tyr Leu Glu
1               5                   10                  15

<210> SEQ ID NO 69
<211> LENGTH: 71
<212> TYPE: PRT
<213> ORGANISM: Artificial Sequence
<220> FEATURE:
<223> OTHER INFORMATION: Synthetic

<400> SEQUENCE: 69

Glu Val Gln Leu Val Glu Ser Gly Gly Gly Leu Val Gln Pro Gly Gly
1               5                   10                  15

Ser Leu Arg Leu Ser Cys Ala Ala Ser Trp Val Arg Gln Ala Pro Gly
            20                  25                  30

Lys Gly Leu Glu Trp Val Ser Arg Phe Thr Ile Ser Arg Asp Asn Ser
        35                  40                  45

Lys Asn Thr Leu Tyr Leu Gln Met Asn Ser Leu Arg Ala Glu Asp Thr
    50                  55                  60

Ala Val Tyr Tyr Cys Ala Arg
65                  70

<210> SEQ ID NO 70
<211> LENGTH: 112
<212> TYPE: PRT
<213> ORGANISM: Artificial Sequence
<220> FEATURE:
<223> OTHER INFORMATION: Synthetic

<400> SEQUENCE: 70
```

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
                20              25                  30

Asn Gly Asn Thr Tyr Leu Glu Trp Tyr Leu Gln Lys Pro Gly Gln Ser
            35                  40                  45

Pro Gln Leu Leu Ile Tyr Lys Ala Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser Arg Leu Gly Pro Ser Phe Gly Gln Gly Thr Lys Leu Glu Ile Leu
            100                 105                 110

<210> SEQ ID NO 71
<211> LENGTH: 70
<212> TYPE: PRT
<213> ORGANISM: Artificial Sequence
<220> FEATURE:
<223> OTHER INFORMATION: Synthetic

<400> SEQUENCE: 71

Asp Ile Val Met Thr Gln Ser Pro Leu Ser Leu Pro Val Thr Pro Gly
1               5                   10                  15

Glu Pro Ala Ser Ile Ser Cys Trp Tyr Leu Gln Lys Pro Gly Gln Ser
                20              25                  30

Pro Gln Leu Leu Ile Tyr Gly Val Pro Asp Arg Phe Ser Gly Ser Gly
            35                  40                  45

Ser Gly Thr Asp Phe Thr Leu Lys Ile Ser Arg Val Glu Ala Glu Asp
        50                  55                  60

Val Gly Val Tyr Tyr Cys
65                  70
```

ANTI-ADDL MONOCLONAL ANTIBODY AND USES THEREOF

CROSS-REFERENCE TO RELATED APPLICATIONS

This application claims priority under 35 USC §119 to U.S. Provisional Application No. 61/364,210, filed Jul. 14, 2011.

FIELD OF THE INVENTION

The present invention relates to monoclonal antibodies for use in the treatment of Alzheimer's disease. The invention also provides compositions comprising monoclonal antibodies and methods of using the compositions as biomarkers or for diagnosing and treating diseases associated with amyloid beta (Aβ) and Aβ-derived diffusible ligands (ADDLs).

BACKGROUND OF THE INVENTION

Alzheimer's disease (AD) is characterized by the progressive loss of cognitive function and the accumulation of amyloid beta (Aβ) plaques in regions associated with learning and memory. While Aβ plaques were once thought to play a central role in the pathogenesis of AD, a growing body of evidence suggests that the Aβ-derived diffusible ligands (ADDLs) may be responsible for the disease-associated neuronal dysfunction and cognitive decline (Walsh and Selkoe, 2004, *Protein Pept. Lett.,* 11: 213-228). ADDLs are small, soluble oligomers of Aβ that are abundant in AD, but not normal, brains (McLean et al., 1999, *Ann. Neurol.,* 46: 860-866; Gong et al., 2003, *Proc. Natl. Acad. Sci. USA,* 100: 10417-10422). In vitro studies have shown that ADDLs, isolated from AD brain or synthetic preparations, bind to a subpopulation of cortical and hippocampal neurons (Gong et al., 2003; Klein et al., 2004, *Neurobiol. Aging,* 25: 569-580; Lacor et al., 2004, *J. Neurosci.,* 24: 10191-10200; Shughrue et al., 2010, *Neurobiol. Aging,* 31: 189-202), while little or no binding was detected with fibrillar or monomer Aβ preparations (Lacor et al., 2004; Hepler et al., 2006, *Biochemistry,* 45: 15157-15167). Furthermore, ADDL binding to neurons can be attenuated with both polyclonal (Gong et al., 2003) and monoclonal antibodies (Lee et al., 2006, *J. Biol. Chem.,* 281: 4292-4299; De Felice et al., 2007, *Neurobiol. Aging* 29: 1334-1347; Shughrue et al., 2010) generated against ADDLs.

In rodent models, the central administration of ADDLs induces deficits in rodent long term potentiation (LTP) and memory formation (Walsh et al., 2002, *Nature,* 416: 535-539; Cleary et al., 2004, *Nat. Neurosci.,* 8: 79-84; Klyubin et al., 2005, *Nat. Med.,* 11: 556-561). The effect of oligomers on LTP was attenuated when ADDLs were co-administered with an anti-Aβ antibody or administered to animals that were vaccinated with the Aβ peptide (Rowan et al, 2004, *Exp. Gerontol.,* 39: 1661-1667). In a transgenic model of AD, such as transgenic mice that produce human amyloid precursor protein (hAPP), age-associated cognitive deficits have been observed with elevated ADDL levels (Westerman et al., 2002, *J. Neurosci.,* 22: 1858-1867; Ashe, 2005, *Biochem. Soc. Trans.,* 33: 591-594; Lee et al., 2006; Lesne et al., 2006, *Nature,* 440: 352-357). When hAPP mice were treated with an anti-ADDL antibody, a significant improvement in cognitive performance was observed without a concomitant decrease in Aβ plaque load (Lee et al., 2006). Together these findings suggest that ADDLs, and not Aβ plaques, are primarily responsible for cognitive impairment and that the use of anti-ADDL antibodies may prove efficacious in the treatment of AD. See also, US2006/0228349; U.S. Pat. No. 7,731,962, WO 2007/050359; US2007/0218499, WO 2006/014478; U.S. Pat. No. 7,700,099; US 2008/01758835, WO 2006/055178.

Accordingly, there is a need for ADDL-selective therapeutic antibodies for the prevention and treatment of AD. The present invention meets this need.

SUMMARY OF THE INVENTION

The present invention is directed to an isolated antibody, or fragment thereof, capable of differentially recognizing a multi-dimensional conformation of one or more amyloid-β derived diffusible ligands (ADDLs) for the treatment of diseases associated with ADDLs, such as Alzheimer's disease (AD). The present invention also provides pharmaceutical compositions comprising the isolated antibody of the invention, either alone or in combination, with one or more therapeutically active agents, carriers, or diluents.

The present invention is also directed to methods of use for the isolated antibody, such as, methods for detecting ADDLs in a sample, for inhibiting assembly of ADDLs, for identifying therapeutic agents that prevents binding of ADDLs to neurons, and for attenuating the symptoms of a disease associated with ADDLs, and as a biomarker for use in the diagnosis of a disease associated with ADDLs or for the detection of ADDLs in a sample.

BRIEF DESCRIPTION OF THE DRAWINGS

FIG. 5 is a graphic representation of the binding and dissociation of anti-ADDL antibodies to immobilized human FcRn when assessed with Biacore™ (GE Healthcare, Piscataway, N.J.). The adjusted sensorgram shows initial binding at pH 6.0 and then the dissociation of antibodies at pH 7.3 from 180 seconds. A report point (Stability) was inserted at 5 seconds after the end of pH 6.0 binding and the "% bound" was calculated as $RU_{Stability}/RU_{Binding}$ (%).

FIG. 6A shows the alignment of the heavy and light chain variable regions for anti-ADDL antibody 19.3 with a human germ line with the complementary determining regions (CDRs) indicated in bold type face.

FIG. 11B; antibody 19.3: FIG. 11C, ring). Immunocytochemical analysis was used to assess the deposition of new material (ADDLs) (FIGS. 11B and 11C).

DETAILED DESCRIPTION OF THE INVENTION

Figure 1:
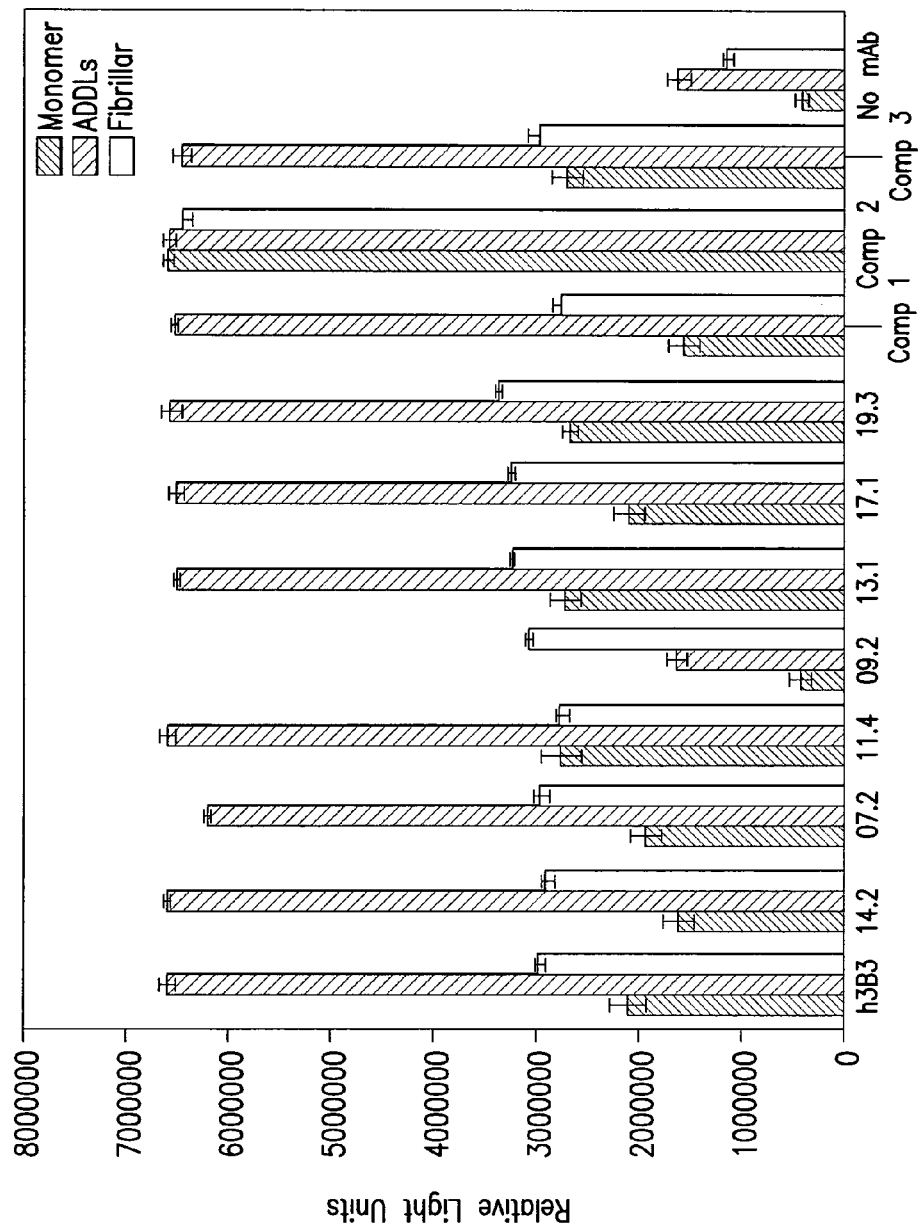
FIG. 1 is a graphic representation of the ELISA binding of a panel of humanized (h3B3) and affinity matured anti-ADDL (14.2, 7.2, 11.4, 9.2, 13.1, 17.1, and 19.3) antibodies and three comparator antibodies (Comp 1, 2, and 3) to monomer Aβ, ADDLs and fibrillar Aβ. The background of this assay was determined by removing the capture antibody from the ELISA (no mAb). Error bars represent standard error of the mean.

The present invention is directed to antibodies, or an antigen binding fragment, that bind amyloid β (Aβ)-derived diffusible ligands (ADDLs), i.e. anti-ADDL antibodies, and attenuate ADDL binding to neurons. Results from a quantitative cell-based assay revealed that anti-ADDL antibodies preferentially bound ADDLs, abated the binding of ADDLs to hippocampal neurons, crossed the blood-brain barrier, and had an improved pharmacokinetic (PK) profile.

In one embodiment the present invention is directed to an isolated antibody, or an antigen binding fragment thereof, that binds amyloid β-derived diffusible ligands (ADDLs) comprising:

(a) a light chain variable region comprising,
(i) a CDR1 having the sequence Arg-Ser-Ser-Gln-Ser-Ile-Val-His-Ser-Asn-Gly-Asn-Thr-Tyr-Leu-Glu (SEQ ID NO: 1),
(ii) a CDR2 having the sequence Lys-Ala-Ser-Asn-Arg-Phe-Ser (SEQ ID NO: 2), and
(iii) a CDR3 having the sequence Phe-Gln-Gly-Ser-Xaa1-Xaa2-Xaa3-Xaa4-Xaa5 (SEQ ID NO: 3), wherein Xaa1 is Arg, Lys or Tyr, Xaa2 is Val, Ala, or Leu, Xaa3 is Pro, His, or Gly, Xaa4 is Ala, Pro, or Val, and Xaa5 is Ser, Gly, or Phe; and
(b) a heavy chain variable region comprising,
(i) a CDR1 having the sequence Gly-Phe-Thr-Phe-Ser-Ser-Phe-Gly-Met-His (SEQ ID NO: 4),
(ii) a CDR2 having the sequence Tyr-Ile-Ser-Arg-Gly-Ser-Ser-Thr-Ile-Tyr-Tyr-Ala-Asp-Thr-Val-Lys-Gly (SEQ ID NO: 5), and
(iii) a CDR3 having the sequence Gly-Ile-Thr-Thr-Ala-Leu-Asp-Tyr (SEQ ID NO: 6).

In another embodiment the present invention is directed to an isolated antibody, or an antigen binding fragment thereof, that binds amyloid β-derived diffusible ligands (ADDLs) comprising:

(a) a light chain variable region comprising,
(i) a CDR1 having the sequence Arg-Ser-Ser-Gln-Ser-Ile-Val-His-Ser-Xaa1-Gly-Xaa2-Thr-Tyr-Leu-Glu (SEQ ID NO: 53), wherein Xaa1 is Asn, Ser, Thr, Ala, Asp or Glu and Xaa2 is Asn, His, Gln, Ser, Thr, Ala, or Asp;
(ii) a CDR2 having the sequence Lys-Ala-Ser-Xaa1-Arg-Phe-Ser (SEQ ID NO: 54), wherein Xaa1 is Asn, Gln, Ser, Thr, or Ala, and
(iii) a CDR3 having the sequence Phe-Gln-Gly-Ser-Arg-Leu-Gly-Pro-Ser (SEQ ID NO: 10); and
(b) a heavy chain variable region comprising,
(i) a CDR1 having the sequence Gly-Phe-Thr-Phe-Ser-Ser-Phe-Gly-Met-His (SEQ ID NO: 4),
(ii) a CDR2 having the sequence Tyr-Ile-Ser-Arg-Gly-Ser-er-Thr-Ile-Tyr-Tyr-Ala-Asp-Thr-Val-Lys-Gly (SEQ ID NO: 5), and
(iii) a CDR3 having the sequence Gly-Ile-Thr-Thr-Ala-Leu-Asp-Tyr (SEQ ID NO: 6).

In another embodiment the present invention is an isolated antibody that binds ADDLs, i.e. an anti-ADDL antibody, or an antigen binding fragment thereof, having a light chain variable region CDR3 that is selected from the group consisting of 17.1, having the sequence Phe-Gln-Gly-Ser-Arg-Val-Pro-Ala-Ser (SEQ ID NO: 7), 14.2, having the sequence Phe-Gln-Gly-Ser-Arg-Val-Pro-Pro-Gly (SEQ ID NO: 8), 13.1, having the sequence Phe-Gln-Gly-Ser-Lys-Ala-His-Pro-Ser (SEQ ID NO: 9), 19.3, having the sequence Phe-Gln-Gly-Ser-Arg-Leu-Gly-Pro-Ser (SEQ ID NO: 10), 7.2, having the sequence Phe-Gln-Gly-Ser-Tyr-Ala-Pro-Pro-Gly (SEQ ID NO: 11), 9.2, having the sequence Phe-Gln-Gly-Ser-Arg-Ala-Pro-Pro-Phe (SEQ ID NO: 12), and 11.4, having the sequence Phe-Gln-Gly-Ser-Arg-Val-Pro-Val-Arg (SEQ ID NO: 13). In a sub-embodiment the light chain variable region CDR3 is SEQ ID NO: 10.

In still another embodiment of the present invention the isolated anti-ADDL antibody further comprises a light chain variable region of SEQ ID NO: 15 and a heavy chain variable region of SEQ ID NO: 17.

In yet another embodiment of the present invention the isolated anti-ADDL antibody further comprises a heavy chain constant region of SEQ ID NO: 21.

In another embodiment of the present invention the isolated anti-ADDL antibody is a monoclonal antibody.

Another embodiment of the present invention is a pharmaceutical composition comprising an isolated anti-ADDL antibody, or an antigen binding fragment thereof, in admixture with a pharmaceutically acceptable carrier.

Another embodiment of the present invention is a method for attenuating binding of ADDLs to a neuron comprising contacting the neuron with an isolated anti-ADDL antibody, or an antigen binding fragment thereof, so that binding of Aβ-derived diffusible ligands to the neuron is attenuated.

Another embodiment of the present invention is a method for inhibiting the assembly of ADDLs comprising contacting a sample containing amyloid β 1-42 peptides with an isolated anti-ADDL antibody, or antigen binding fragment thereof, thereby inhibiting the assembly of ADDLs.

Another embodiment of the present invention is a method for inhibiting the phosphorylation of tau protein at Ser202/Thr205 comprising contacting a sample containing a tau protein with an isolated anti-ADDL antibody, or an antigen binding fragment thereof, thereby inhibiting the phosphorylation of tau protein at Ser202/Thr205.

Another embodiment of the present invention is a method for attenuating the symptoms of a disease associated with ADDLs comprising administering an effective amount to a patient in need thereof of the pharmaceutical composition comprising an isolated anti-ADDL antibody, or an antigen binding fragment thereof.

Another embodiment of the present invention is a method for identifying a putative therapeutic agent that attenuates the binding of amyloid β-derived diffusible ligands (ADDLs) to neurons comprising:

(a) contacting a composition comprising a neuron with ADDLs in the presence of an agent;

(b) contacting the composition with the isolated anti-ADDL antibody, or an antigen binding fragment thereof; and (c) detecting the amount of antibody or antigen binding fragment bound in the presence of the agent, wherein a decrease in the amount of antibody or antigen binding fragment bound in the presence of the agent as compared to the amount of antibody bound in the absence of the agent indicates that the agent is a putative therapeutic agent for attenuating binding of ADDLs to neurons.

Another embodiment of the present invention is a method for detecting ADDLs in a sample comprising contacting a sample with an isolated anti-ADDL antibody, or an antigen binding fragment thereof, and determining the presence of a complex comprising the ADDLs and said antibody or antigen binding fragment.

Another embodiment of the present invention is a method for diagnosing a disease associated with ADDLs comprising contacting a sample with an isolated anti-ADDL antibody, or an antigen binding fragment thereof, and determining the presence of a complex comprising the ADDLs and said isolated antibody or antigen binding fragment, wherein the presence of said complex is diagnostic of a disease associated with ADDLs.

Still another embodiment of the present invention is a kit for detecting ADDLs comprising an isolated anti-ADDL antibody, or an antigen binding fragment thereof, that binds ADDLs.

Monoclonal antibodies, which differentially recognize multi-dimensional conformations of Aβ-derived diffusible ligands (ADDLs) are known in the art (see, U.S. Pat. No. 7,780,963, U.S. Pat. No. 7,731,962, and U.S. Pat. No. 7,811,563, all of which are incorporated herein by reference in their entirety), and have been shown to reduce ADDL binding to neurons in cell based assays. Anti-ADDL antibodies can distinguish between Alzheimer's disease (AD) and control human brain extracts, can identify endogenous oligomers in AD brain slices and on hippocampal cells, and can neutralize endogenous and synthetic ADDLs in solution. Anti-ADDL antibodies specifically bind one or more multi-dimensional conformations of ADDLs, bind particular ADDLs derived from the oligomerization of Aβ42, while having reduced affinity for other Aβ peptides, including Aβ1-40.

The present invention is directed to anti-ADDL antibodies, specifically antibodies 17.1, 14.2, 13.1, 19.3, 19.3T33, 19.3S33, 7.2, 9.2, and 11.4, that preferentially bind ADDLs and that have been characterized as to their specificity and selectivity for ADDLs. Importantly, the specificity and selectivity of these anti-ADDL antibodies of the present invention was not predictable from the linear epitope of Aβ to which they bound, nor was this activity predictable from their ability to detect ADDLs by Western blot, or from their ability to detect immuno-stained ADDLs bound to neurons. Moreover, the differential ability of the anti-ADDL antibodies of the present invention to neutralize ADDLs and block binding to primary hippocampal neurons supports the belief that anti-ADDL antibodies act through binding to a more relevant, conformational epitope, which prevents ADDL binding to neurons. One embodiment of the present invention, anti-ADDL antibody 19.3, not only blocked the binding of ADDLs to primary neurons, but also abated ADDL-induced changes to hippocampal spine morphology, an indication that the impedance of ADDL-neural binding has significant physiological ramifications, for example, neuronal survival, neuronal connectivity and signal transduction. Anti-ADDL antibody 19.3 also had an improved pharmacokinetic (PK) profile, as compared with a previously known anti-ADDL antibody, 3B3, when assessed in both in vitro and in vivo models. In addition, when administered to transgenic mice that over-express a human form of amyloid precursor protein (hAPP), anti-ADDL antibody 19.3 was shown to penetrate the blood-brain-barrier and concentrate in the brain. Since ADDLs are localized in the brain and act there to adversely affect neuronal function, one of skill in the art would appreciate and recognize that the penetration and concentration of antibody in the brain would be beneficial for immunotherapy. Taken together, these data demonstrate that selective anti-ADDL antibodies, such as antibody 19.3, can block the binding of ADDLs to hippocampal neurons, which are critically involved in learning and memory.

The utility of anti-ADDL antibodies for the treatment of AD is based on a growing body of evidence that suggests that ADDLs, and not amyloid plaques per se, play a fundamental role in the cognitive decline associated with this disease (Walsh and Selkoe, 2004, *Protein Pept. Lett.,* 11: 213-228). ADDLs are elevated in the AD brain and induce deficits in behavioral and electrophysiological endpoints when centrally administered to rodents (Walsh, et al., 2002, *Nature,* 416: 535-539; Cleary, et al., 2004, *Nat. Neurosci.,* 8: 79-84; Klyubin, et al., 2005, *Nat. Med.,* 11: 556-561; Balducci, et al., 2010, *Proc. Natl. Acad. Sci. USA,* 107: 2295-2300). Deficits in learning and memory have also been observed in a hAPP expressing mouse model, with the onset of impairment associated with elevated ADDL levels (Westerman, et al., 2002, *J. Neurosci.,* 22: 1858-1867; Ashe, 2005, *Biochem. Soc. Trans.,* 33: 591-594; Lee, et al., 2005, *J. Biol. Chem.,* 281: 4292-4299; Lesne, et al., 2006, *Nature,* 440: 352-357). While the cellular and sub-cellular events that mediate these effects on cognition are not fully understood, it is clear that ADDLs bind to the synaptic terminals localized on the dendritic processes of hippocampal neurons (Lacore, et al., 2004, *J. Neurosci.,* 24: 10191-1022) and alter the morphology and number of dendritic spines (Lacor et al., 2007, *J. Neurosci.,* 27: 796-807; Shankar, et al., 2007, *J. Neurosci.,* 27: 2866-2875; Shughrue, et al., 2010, *Neurobiol. Aging,* 31: 189-202). The finding that ADDLs bind to both GABAergic and glutamate neurons in the hippocampus (Shughrue, et al., 2010), neurons critically involved in learning and memory, which results in the internalization of AMPA receptors (Zhao, et al., 2010, *J. Biol. Chem.*, 285: 7619-7632) further supports the belief that ADDLs directly or indirectly modulate these neurotransmitter systems (see, for example, Venkitaramani, et al., 2007, *J. Neurosci.*, 27: 11832-11837).

Figure 2:
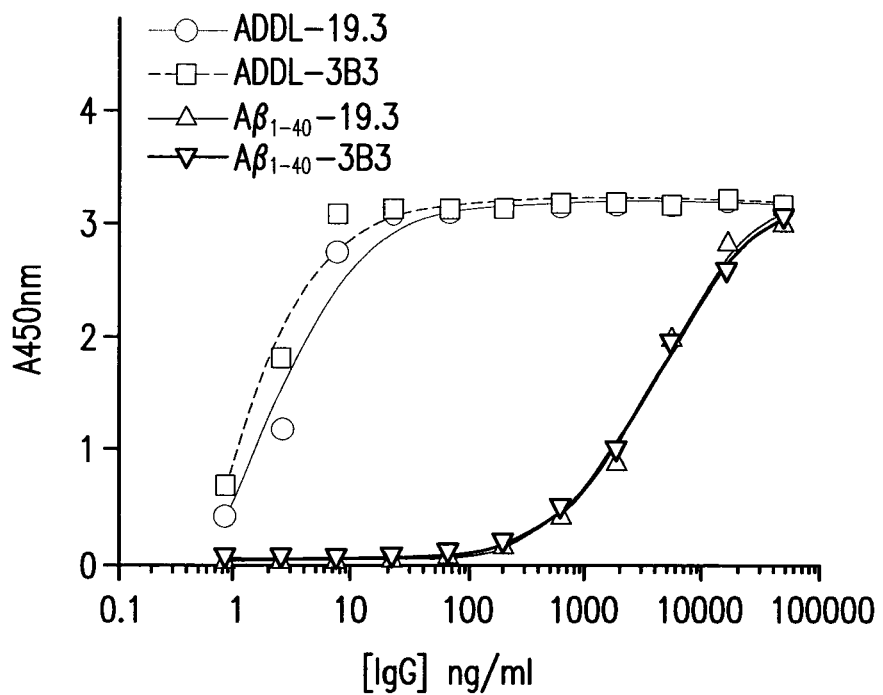
FIG. 2 is a graphic representation of the ELISA binding of anti-ADDL antibody 19.3 and antibody 3B3 to ADDLs or monomer Aβ ($Aβ_{1-40}$) evaluated with an 11 point titration curve.
Figure 3:
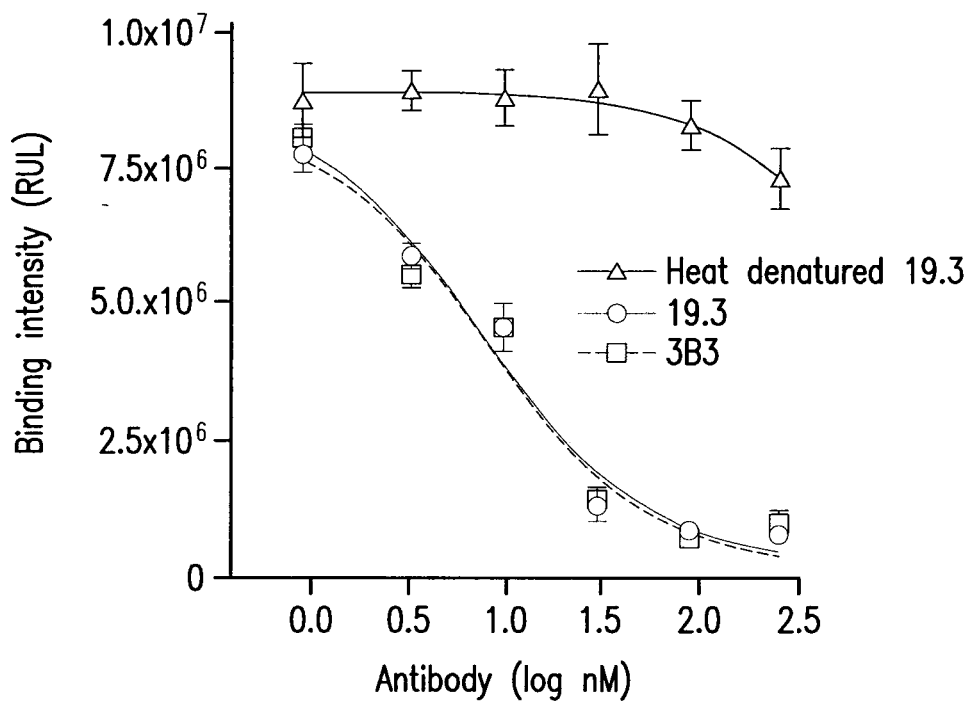
FIG. 3 is a graphic representation of the ability of anti-ADDL antibody 19.3 and 3B3 to block ADDL binding to primary hippocampal neuronal cells after pre-incubation with increasing concentration of the antibody. The ability of anti-ADDL antibody 19.3 to block ADDL binding to neurons was attenuated after heat denaturing of the antibody. Error bars represent standard error of the mean.

In the present invention, a panel of anti-ADDL antibodies derived from anti-ADDL antibody, 3B3 (U.S. Pat. No. 7,780, 963 and U.S. Pat. No. 7,811,563, which are hereby incorporated by reference in their entirety), were assessed for their ability to block ADDL binding to primary hippocampal neurons. Selected monoclonal antibodies were then humanized and affinity matured for further characterization. Lead antibodies, selected for their ability to bind to ADDLs, were further assessed at a single concentration using a three-pronged ELISA to determine antibody binding to monomer Aβ, ADDLs, and fibrillar Aβ. As shown in FIG. 1, six of the seven affinity matured anti-ADDL antibodies, specifically antibodies 14.2, 7.2, 11.4, 13.1, 17.1, and 19.3 were ADDL preferring, when compared with monomer Aβ and fibrillar Aβ. Subsequently an eleven point titration curve and ELISA were used to ascertain the binding affinity of anti-ADDL antibodies to ADDLs and monomer Aβ ($A\beta_{1-40}$) over a broad range of concentrations. As shown in FIG. 2, the anti-ADDL antibodies 3B3 and 19.3 were highly ADDL selective. In addition, antibodies were compared in a cell-based binding assay to determine the ability of antibodies to block ADDL binding to neurons. As shown in FIG. 3, ADDLs, pre-incubated with increasing concentrations of anti-ADDL antibodies 3B3 and 19.3, were added to primary hippocampal neurons, and a titration curve was used to show quantitatively the ability of the antibody to block ADDL binding to neurons. Taken together, these results show that anti-ADDL antibodies profoundly attenuate neuronal binding in a cell-based format.

Figure 4A:
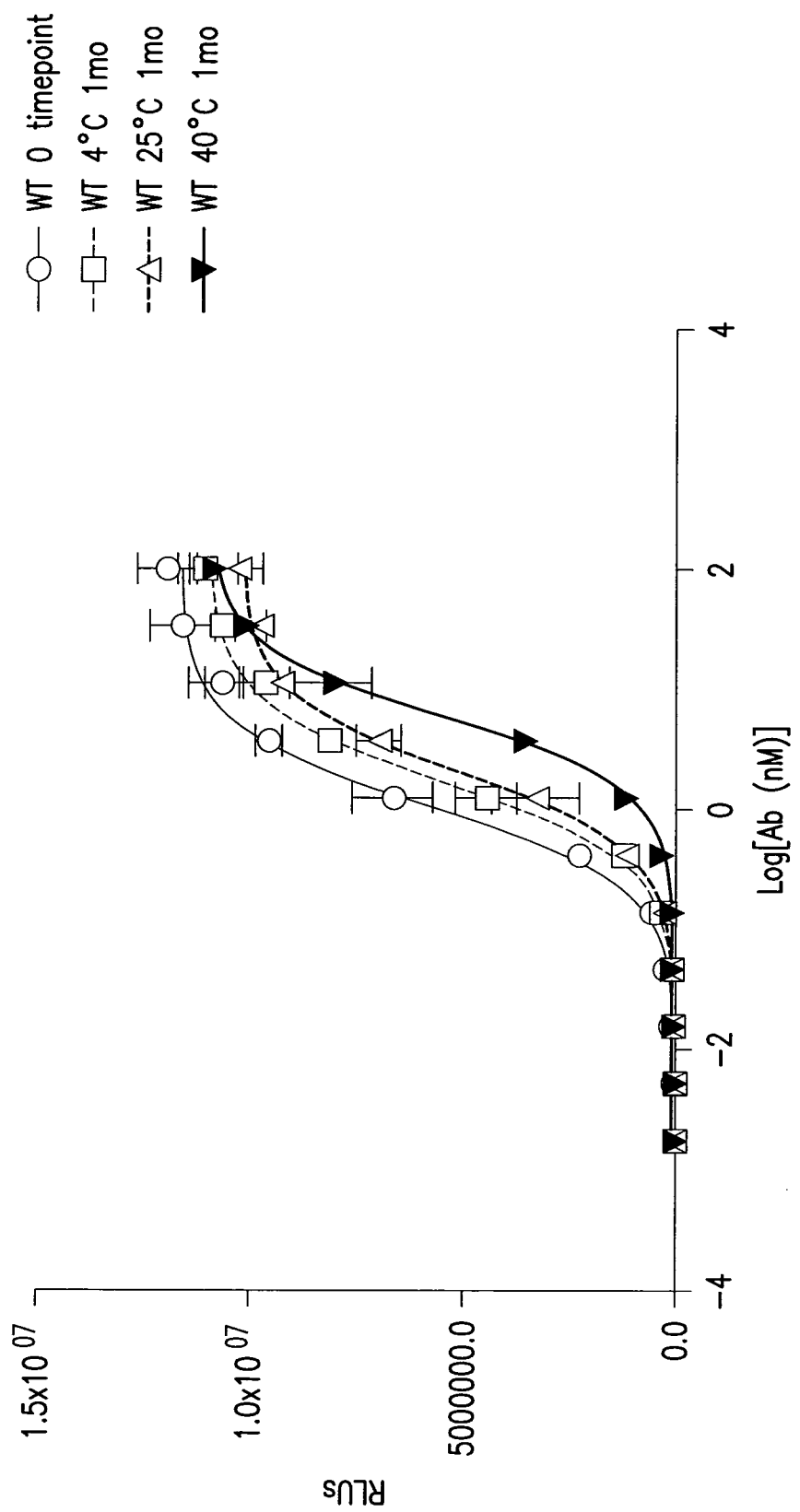
FIGS. 4A-4C are graphic representations of the ELISA binding to ADDLs of the anti-ADDL antibody 19.3 (designated as WT in FIG. 4A) and two 19.3-derived anti-ADDL antibodies (FIGS. 4B and 4C) after incubation up to one month at varying temperatures to evaluate antibody stability. The 19.3-derived anti-ADDL antibodies comprised a single amino-acid substitution of Asn33 within light chain CDR1 to either Ser33 (19.3S33) or Thr33 (19.3T33) (SEQ ID NOS: 55 and 56, respectively). Substitution of Asn33 with either S33 (FIG. 4B) or T33 (FIG. 4C) resulted in improved antibody stability versus the parental 19.3 antibody.
Figure 4B:
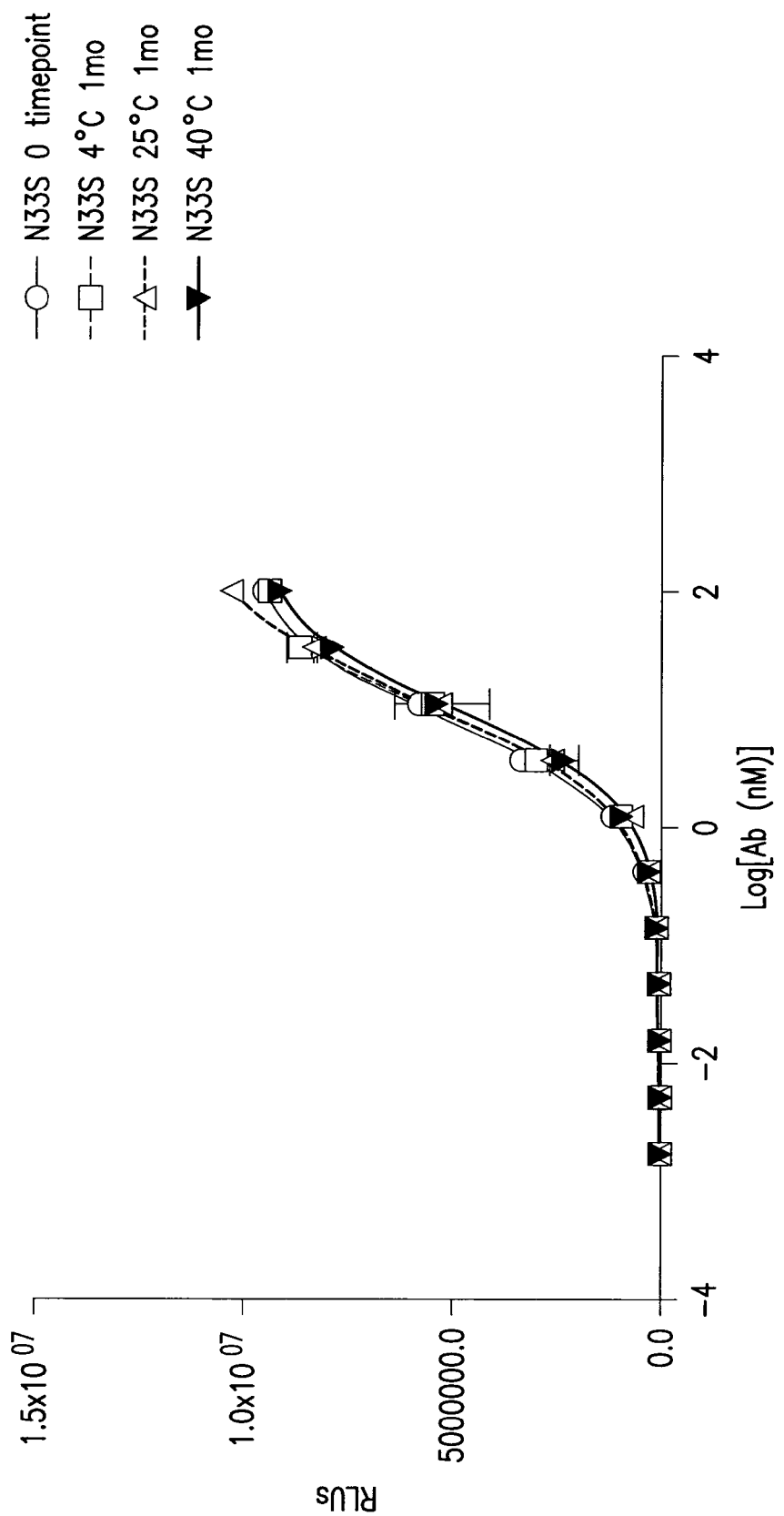
Figure 4C:
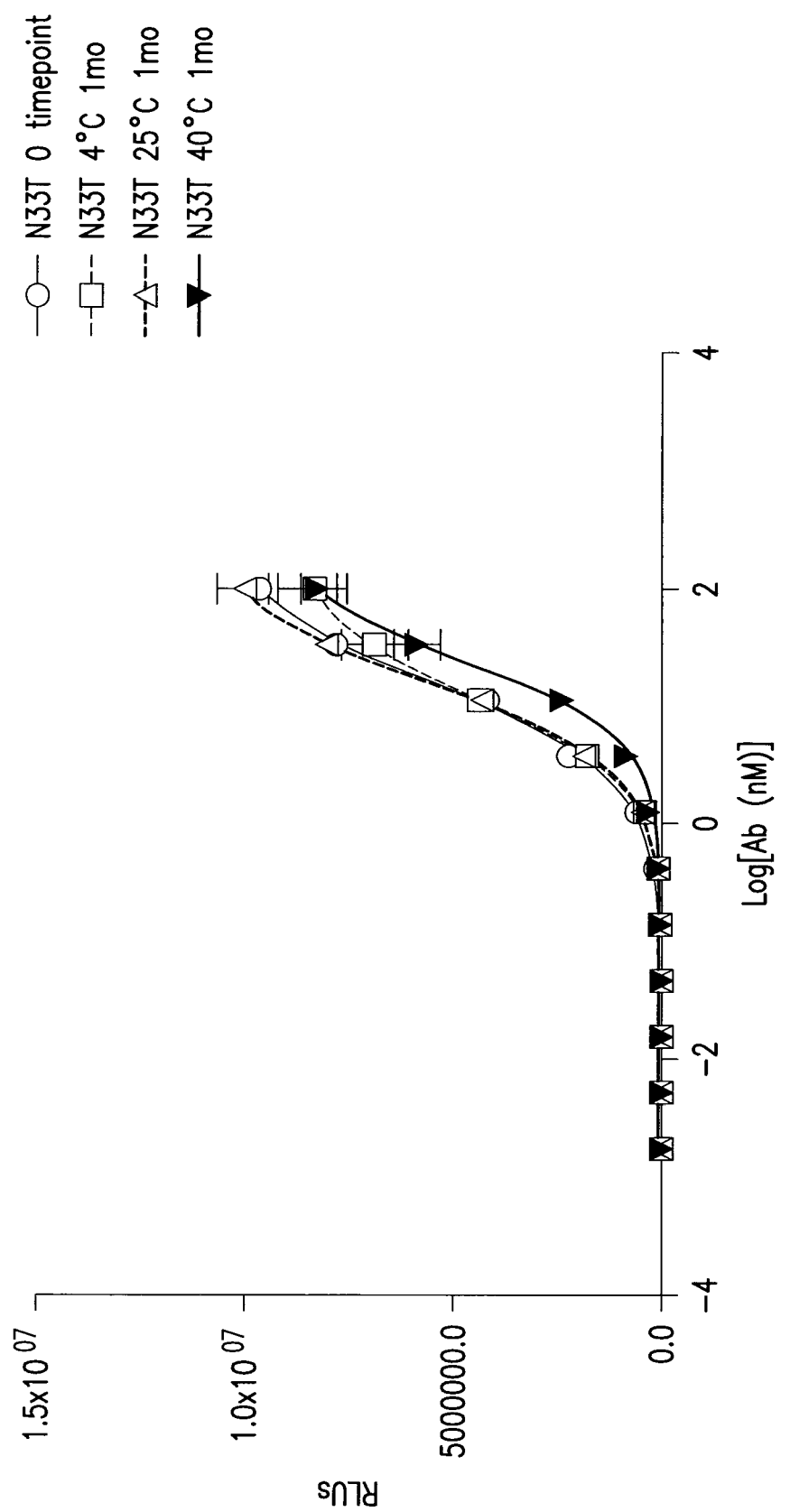

An assessment of the amino acid sequence was conducted to identify potential sites of deamidation. Asparagine and aspartic acid residues present in the CDRs of therapeutic antibodies are known to undergo deamidation and isoaspartate formation (Valsak and Ionescu, 2008, *Curr. Pharm. Biotech.*, 9:468-481; Aswad et al., 2000, *J. Pharm. Biomed. Anal.*, 21:1129-1136), the formation of which can alter the binding potency of an antibody and, in turn, reduce antibody effectiveness for use as a therapeutic. Thus, those of skill in the art would recognize and appreciate that the presence of an asparagine or an aspartic acid within the CDRs for the 19.3 antibody would not be desirable. Accordingly, Applicants altered the asparagine residue at position 33 of the light chain CDR1 to optimize the stability of the anti-ADDL antibody 19.3 (Table 4B). Derivatives of the 19.3 antibody were produced with the substitution of serine (SEQ ID NO: 55), threonine (SEQ ID NO: 56), or glutamic acid (SEQ ID NO: 67) for the asparagine at position 33 (SEQ ID NO: 1) in CDR1. The substitution of aspartic acid (SEQ ID NO: 68) for the asparagine as position 33 was also generated as a control. These changes will remove the possibility of deamidation of asparagine at position 33 in CDR1. The 19.3 derivatives were generated as described in Example 3 and characterized as described in Example 4 as to derivatives with the serine (SEQ ID NO: 55), threonine (SEQ ID NO: 56), glutamic acid (SEQ ID NO: 67), and aspartic acid (SEQ ID NO: 68) substitutions, to evaluate the stability of the new constructs. As shown in FIGS. 4B and 4C, respectively, two representative derivatives, 19.3S33 (SEQ ID NO: 55) and 19.3T33 (SEQ ID NO: 56), had enhanced binding stability following a one-month incubation at varying temperatures. Other amino acid substitutions in the light chain CDR1 for the asparagine at positions 33 and 35 (SEQ ID NO: 53) and in the light chain CDR2 for the asparagine at position 58 position (SEQ ID NO: 54) are proposed in Tables 4B and 4C for further evaluation.

Figure 7:
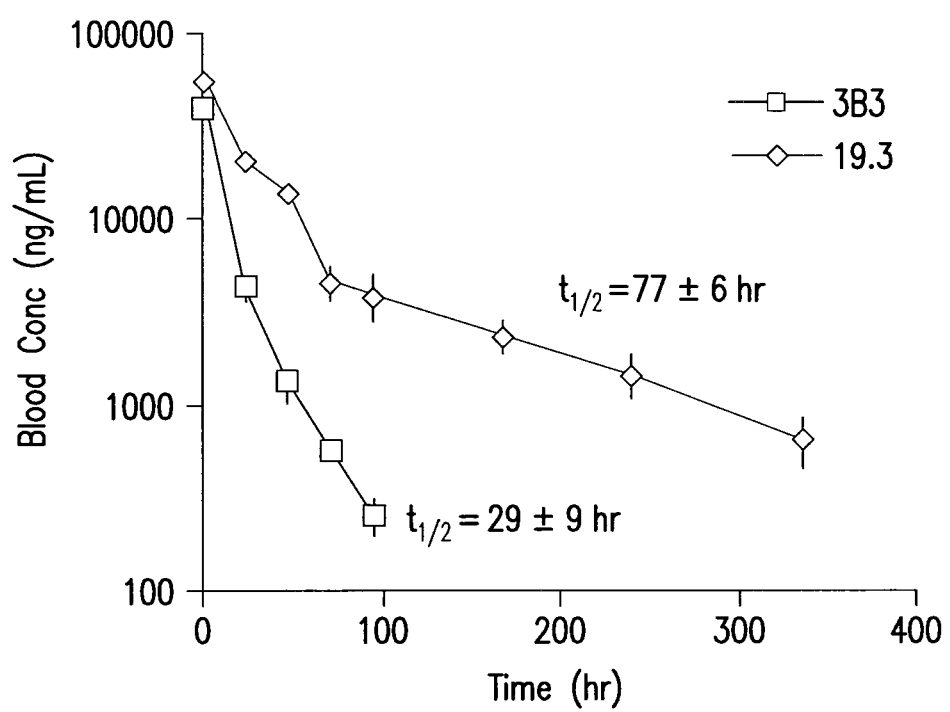
FIG. 7 is a graphical representation of the pharmacokinetic (PK) profile of anti-ADDL antibodies 19.3 and 3B3 evaluated in heterozygous 276 human FcRn mice (Jackson Laboratory (Bar Harbor, Me.) following a single 10 mg/kg intravenous (IV) administration. The concentration of antibody was measured at various time intervals to determine the half-life ($t_{1/2}$) of free anti-body (19.3: 77±6 hours; 3B3 respectively: 29±9 hours).

To determine the pharmacokinetics of the affinity matured anti-ADDL antibodies of the present invention, a series of in vitro and in vivo studies were conducted. The binding of antibodies to the FcRn receptor at pH 6.0 has been shown to be predictive of antibody half-life in humans (Zalevsky, et al., 2010, *Nat. Biotech.*, 28(2): 157-159) and at pH 7.3 (U.S. Ser. No. 61/307,182) The binding and dissociation of the anti-ADDL antibodies of the present invention to immobilized human FcRn was assessed with a label free interaction analysis, such as that offered by Biacore™ Life Sciences, Biacore™ T-100 (GE Healthcare, Piscataway, N.J.). An adjusted sensorgram is used to show the initial binding at pH 6.0 and then the dissociation of antibodies at pH 7.3 from 180 seconds. A report point (Stability) was inserted at 5 seconds after the end of pH 6.0 binding and the "% bound" was calculated as $RU_{Stability}/RU_{Binding}$ (%). As shown in FIG. 5, the off-rate for humanized 3B3 was markedly slower than the seven anti-ADDL antibodies of the present invention, which included antibody 19.3, and three comparator antibodies. In that a slow off-rate is thought to be an indicator of poor in vivo PK, an additional in vivo study was conducted in transgenic FcRn mice (heterozygous 276 human FcRn mice, Jackson Laboratories, Bar Harbor, Me.). When the transgenic FcRn mice were given 10 mg/kg intravenously (IV) of either anti-ADDL antibody 3B3 or 19.3, a significant difference in pharmacokinetics was determined. As shown in FIG. 7, the half-life ($t_{1/2}$) of anti-ADDL antibody 3B3 was relatively short (29±9 hours), which was consistent with the prediction from the in vitro Biacore™ data, while the half-life for anti-ADDL antibody 19.3 was significantly longer (77±6 hours). Generally, poor PK, as seen with antibody 3B3, would preclude further development of an antibody for use as a therapeutic due to its short bioavailability.

Figure 8:
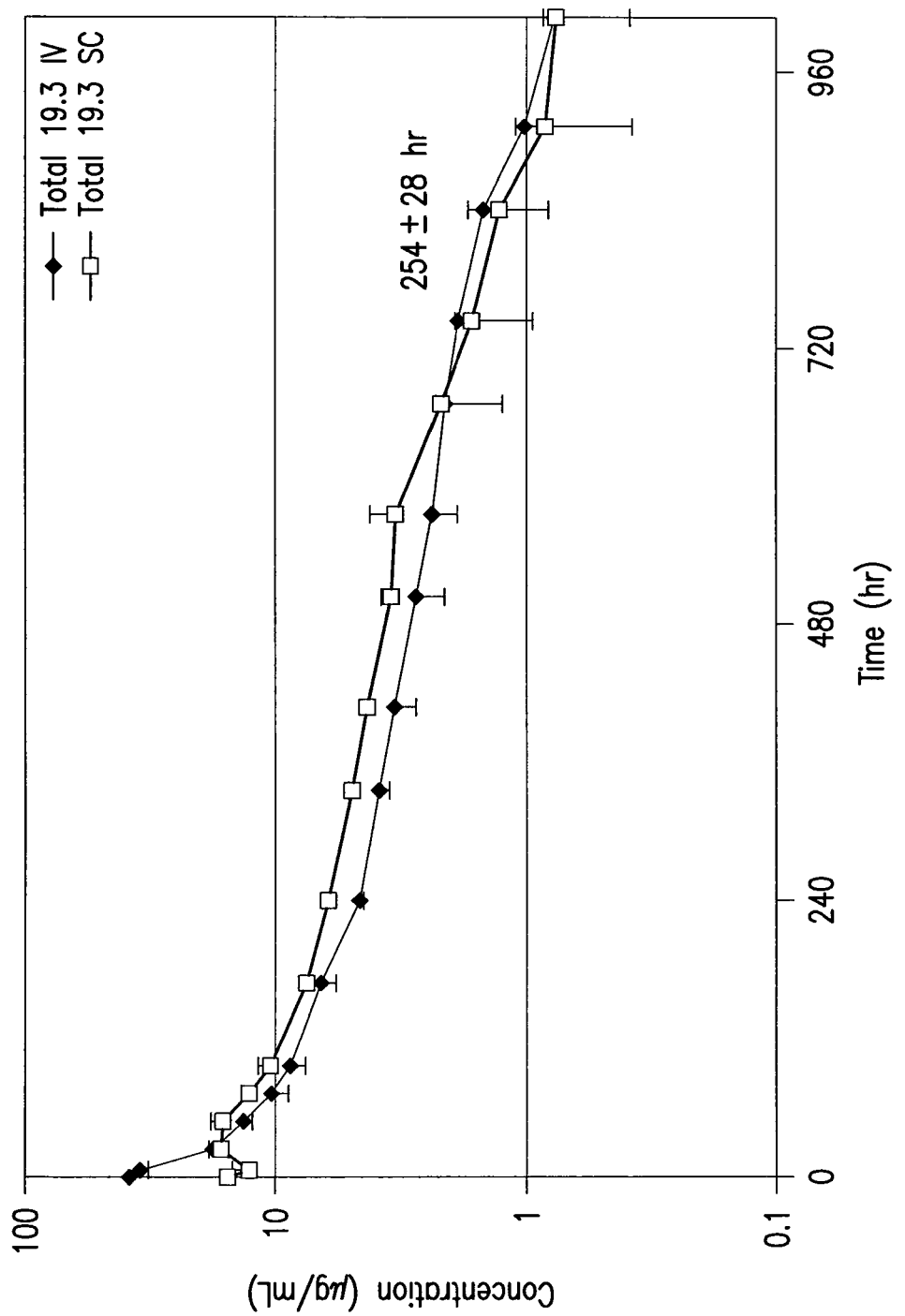
FIG. 8 is a graphical representation of the PK of anti-ADDL antibody 19.3 (in serum) assessed in six rhesus monkeys following administration of a bolus intravenous (IV) or subcutaneous (SC) dose of 5 mg/kg. A half-life ($t_{1/2}$) of 254±28 (274±9) hours was determined after IV administration and 204±49 (219±52) hours after SC dosing.
Figure 9:
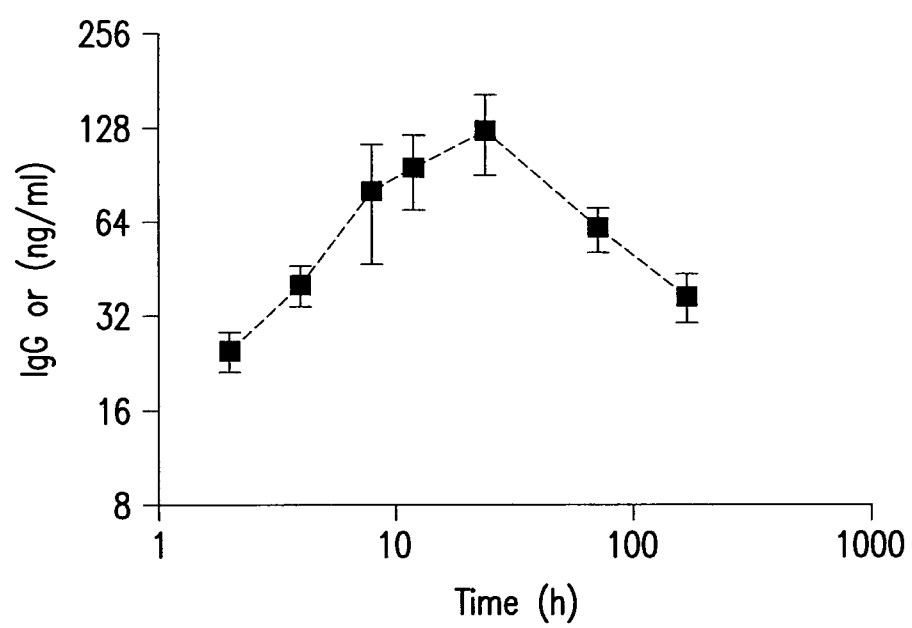
FIG. 9 is a graphical representation of the PK of anti-ADDL antibody 19.3 assessed in primate (three male rhesus monkeys) cerebrospinal fluid (CSF) using a cisterna *magna* ported rhesus model following administration of a bolus IV dose of 5 mg/kg. At about 48 hours post dose, the anti-ADDL antibody 19.3 was present in the CSF at 0.1% of the concentration in serum.

To confirm the predicted half-life of anti-ADDL antibody 19.3 in primates, a primate pharmacokinetics study was conducted for the antibody in a cohort of cisterna magna ported rhesus monkeys. The animals were dosed with a single intravenous (IV) bolus or subcutaneous (SC) injection of anti-ADDL antibody 19.3 (5 mg/kg) and blood samples collected after antibody administration. Concurrently, CSF samples were collected from the cisterna magna port at timed intervals and the concentration of anti-ADDL antibody 19.3 in serum and CSF was determined with an anti-human IgG ELISA assay. When the animals were administered anti-ADDL antibody 19.3 by a single IV bolus injection a $t_{1/2}$ of 254±28 hours (FIG. 8) was observed, while a $t_{1/2}$ of 204±49 hours was observed for the subcutaneous administration. In addition, Applicants found that anti-ADDL antibody 19.3 was able to cross into the primate CSF, where it increased in concentration during the first 48 hours and peaked at about 0.1% of the antibody dosed (FIG. 9).

Figure 10A:
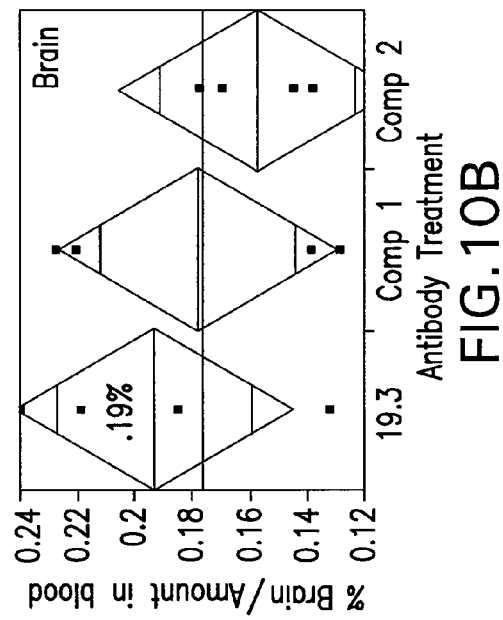
FIGS. 10A-10D are representations of the ability of anti-ADDL antibody 19.3, versus two comparator antibodies (Comp 1 and Comp2), to cross the blood-brain-barrier in a transgenic mouse model that over-expresses human amyloid precursor protein (hAPP). Mice were injected intravenously (IV) with $^{125}$I-labeled anti-ADDL antibody 19.3, or a comparator antibody, and the blood, CSF and brain samples were collected two hours post-dose. Upon assessment of the radioactivity distribution, 0.02% of anti-ADDL antibody 19.3 was present in the CSF (FIG. 10A), while 0.19% was seen in the brain (FIG. 10B). Similar levels were seen with the two comparator antibodies. Immunocytochemical analysis demonstrated localization of anti-ADDL antibody 19.3 (FIG. 10C, arrows) and a concentration of anti-ADDL antibody 19.3 was visible with plaques (FIG. 10D). The anti-ADDL antibody 19.3 was able to penetrate into the brain and bind ADDLs.
Figure 10B:
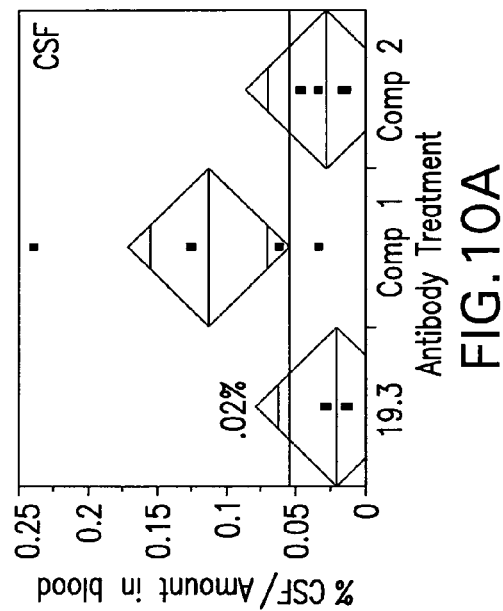
Figure 10D:
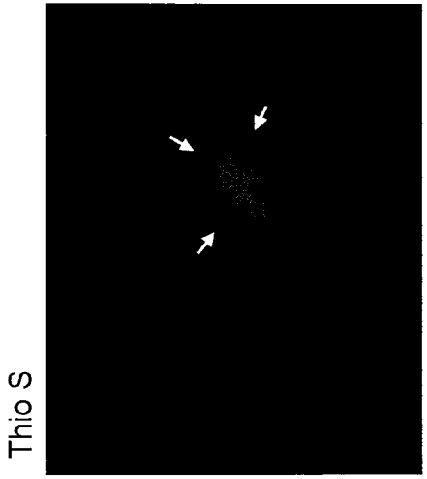

In an attempt to ascertain the quantity of antibody that penetrates the blood-brain-barrier and enters the CSF and brain, anti-ADDL antibody 19.3 and two comparator antibodies (Comp 1 and Comp 2) were $^{125}$I-labeled and administered to aged (twelve-month old) mice that over-express hAPP, a rodent model for AD. Two hours after IV dosing about 0.02% of antibody 19.3 was seen in the CSF (FIG. 10A), while about 0.19% of antibody 19.3 was seen in the brain (FIG. 10B). Similar levels were seen for the two comparator antibodies (FIGS. 10A and 10B). When immunocytochemical analysis was carried out on brain sections of the dosed mice and the localization of anti-ADDL antibody 19.3 was determined (arrow in FIG. 10C), a concentration of the antibody associated with the deposition of Aβ into plaques was observed (FIG. 10D). This demonstrated that the anti-ADDL antibody 19.3 penetrated into the CSF and was concentrated in the brain. Recently it was shown that exogenous ADDLs were deposited into plaques when administered to mice that over express hAPP (Gaspar, et al., 2010, *Exp. Neurol.*, 223: 394-400). Thus, the findings herein confirmed that the localized anti-ADDL antibody 19.3 bound to circulating ADDLs associated with plaques.

Figure 11A:
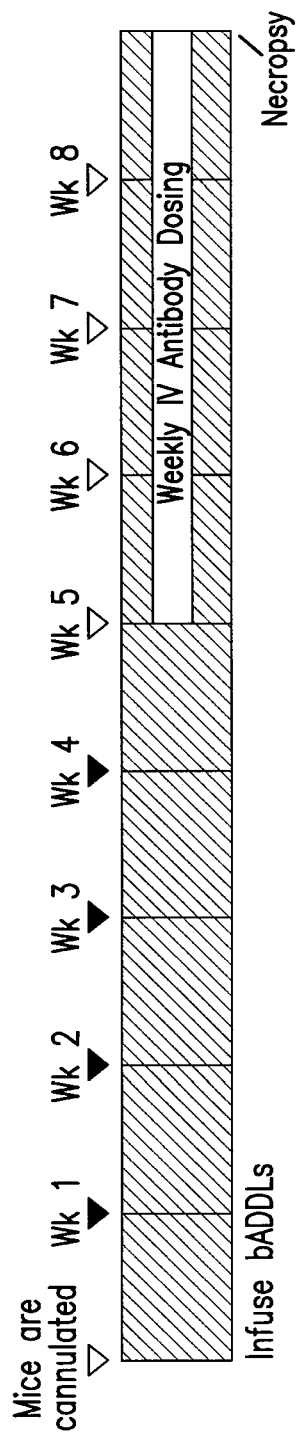
FIGS. 11A-11C are representations of the ability of anti-ADDL antibody 19.3 to block the deposition of ADDLs into growing plaques in a transgenic mouse model that over-expresses hAPP. Biotinylated ADDLs (bADDLs) infused into the hippocampus of 12-month-old mice for four weeks (one injection per week) (FIG. 11A) labeled existing plaques (vehicle alone.
Figure 11B:
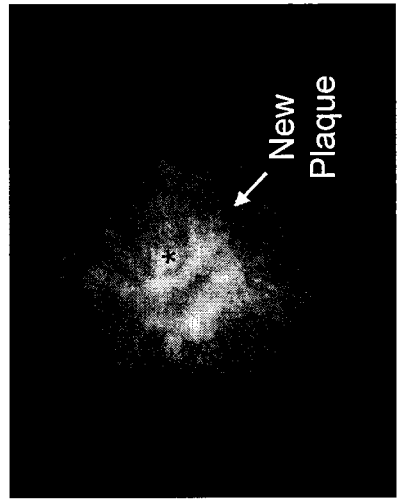
Figure 11C:
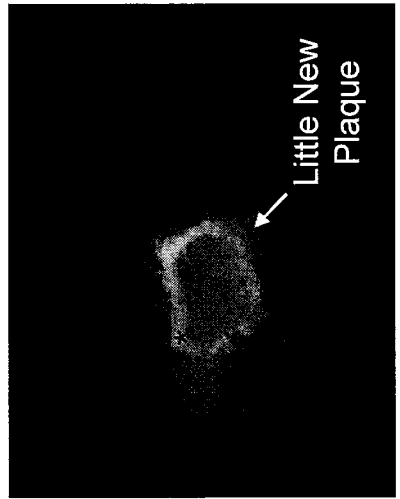

To further evaluate the in vivo efficacy of anti-ADDL antibodies, the ability of antibody 19.3 to block the deposition of ADDLS into growing plaques was assessed in hAPP transgenic mice following four weekly infusions of biotinylated ADDLs (bADDLs) into the hippocampus of 12-month old mice to label existing plaques (FIG. 11A). The animals then received four weekly intravenous infusions of antibody 19.3 (FIG. 11A). The deposition of new material (ADDLs) into growing plaques was assessed by immunocytochemical analysis. As seen in FIGS. 11B and 11C, anti-ADDL antibody 19.3 significantly reduced the deposition of ADDLs into the periphery of existing plaques (FIG. 11C) as compared to mice treated with vehicle alone (FIG. 11B). Taken together, these results demonstrated that an anti-ADDL antibody, specifically the 19.3 antibody, was able to cross the blood-brain-barrier, bind ADDLs, and block the deposition of new material into growing plaques.

ADDL binding may also have long-term effects on neurons. Recent studies have shown that ADDL binding to hippocampal neurons can initiate a signaling cascade that results in the phosphorylation of tau (De Felice, et al., 2006, *Neurobiol. Aging*, 29: 394-400). One component of this signaling cascade, GSK-3β, has also been shown to be modulated by ADDL binding in vivo and in vitro (Ma, et al., 2006, *J. Neurosci. Res.*, 83: 374-384). Ma, et al., 2006, found that passive immunization of hAPP mice with an antibody that reduced ADDLs, also reduced GSK-3β levels and phosphorylation of tau in the cortex. This finding supports a link between Aβ and phosphorylated tau and suggests that ADDL binding may trigger events that lead to the intracellular aggregation of tau. Further, the data suggests that antibodies that prevent the binding of ADDLs to neurons and the associated loss of synaptic spines, such as the antibodies of the present invention could ameliorate the cognitive and/or pathological outcomes associated with Alzheimer's disease and related diseases.

Monoclonal antibodies, which differentially recognize multi-dimensional conformations of Aβ-derived diffusible ligands, i.e., ADDLs, have now been generated. These antibodies were humanized and, in some embodiments, affinity-matured. The antibodies advantageously distinguish between Alzheimer's disease and control human brain extracts, and identify endogenous oligomers in Alzheimer's disease brain slices and in cultured hippocampal cells. Further, the antibodies of the present invention neutralize endogenous and synthetic ADDLs in solution. So-called "synthetic" ADDLs are produced in vitro by mixing purified Aβ1-42 under conditions that generate ADDLs. See, U.S. Pat. No. 6,218,506. The antibodies disclosed herein exhibit a high degree of selectivity for ADDLs, with minimal detection of monomer Aβ species. Moreover, these antibodies differentially block the ability of ADDL-containing preparations to bind primary cultures of rat hippocampal neurons and immortalized neuroblastoma cell lines, and also block ADDL assembly. This finding demonstrates that these antibodies possess a differential ability to recognize a multi-dimensional conformation of ADDLs despite similar linear sequence recognition and affinities. Since ADDLs are known to associate with a subset of neurons and disrupt normal neuronal function, the antibodies of this invention find use in the prevention of ADDL binding to neurons and the assembly of ADDLs and, in turn, can be used for the treatment of ADDL-related diseases including Alzheimer's disease.

Accordingly, one embodiment of the present invention is an isolated antibody that differentially recognizes one or more multi-dimensional conformations of ADDLs. An "isolated" antibody of the present invention refers to an antibody which is substantially free of other antibodies. However, the molecule may include some additional agents or moieties which do not deleteriously affect the basic characteristics of the antibody (for example, binding specificity, neutralizing activity, etc.).

An antibody which is capable of specifically binding one or more multi-dimensional conformations of ADDLs, binds particular ADDLs derived from the oligomerization of Aβ1-42, but does not cross-react with other Aβ peptides, namely Aβ1-12, Aβ1-28, Aβ1-40, and Aβ12-28 as determined by western blot analyses as disclosed herein, and preferentially binds ADDLs in solution. Specific binding between two entities generally refers to an affinity of at least $10^6$, $10^7$, $10^8$, $10^9$, or $10^{10}$ M$^{-1}$. Affinities greater than $10^8$ M$^{-1}$ are desired to achieve specific binding.

In particular embodiments, an antibody that is capable of specifically binding a multi-dimensional conformation of one or more ADDLs is also raised against, i.e., an animal is immunized with, multi-dimensional conformations of ADDLs. In other embodiments, an antibody that is capable of specifically binding a multi-dimensional conformation of one or more ADDLs is raised against a low n-mer-forming peptide such as Aβ1-42[Nle35-Dpro37].

The term "epitope" refers to a site on an antigen to which B and/or T cells respond or a site on a molecule against which an antibody will be produced and/or to which an antibody will bind. For example, an epitope can be recognized by an antibody defining the epitope.

A linear epitope is an epitope wherein an amino acid primary sequence comprises the epitope recognized. A linear epitope typically includes at least 3, and more usually, at least 5, for example, about 6 to about 10 amino acids in a unique sequence.

A conformational epitope, in contrast to a linear epitope, is an epitope wherein the primary sequence of the amino acids comprising the epitope is not the sole defining component of the epitope recognized (for example, an epitope wherein the primary sequence of amino acids is not necessarily recognized by the antibody defining the epitope). Typically a conformational epitope encompasses an increased number of amino acids relative to a linear epitope. With regard to recognition of conformational epitopes, the antibody recognizes a three-dimensional structure of the peptide or protein. For example, when a protein molecule folds to form a three-dimensional structure, certain amino acids and/or the polypeptide backbone forming the conformational epitope become juxtaposed enabling the antibody to recognize the epitope. Methods of determining conformation of epitopes include but are not limited to, for example, x-ray crystallography, two-dimensional nuclear magnetic resonance spectroscopy and site-directed spin labeling and electron paramagnetic resonance spectroscopy. See, for example, Epitope Mapping Protocols in Methods in Molecular Biology (1996) Vol. 66, Morris (Ed.).

Amyloid β-derived diffusible ligands or ADDLs refer to soluble oligomers of Aβ1-42 which are desirably composed of aggregates of less than eight or nine Aβ1-42 peptides and are found associated with Alzheimer's disease. This is in contrast to high molecular weight aggregation intermediates, which form strings of micelles leading to fibril formation.

As exemplified herein, the antibodies of the present invention bind or recognize at least one multi-dimensional conformation of an ADDL. In particular embodiments, the antibodies bind at least two, at least three, or at least four multi-dimensional conformations of an ADDL. Multi-dimensional conformations of ADDLs are intended to encompass dimers, trimers, tetramers pentamers, hexamers, heptamers, octamers, nonamers, decamers, etc. as defined by analysis via SDS-PAGE. Because trimer, tetramer, etc. designations can vary with the assay method employed (see, e.g., Bitan, et al., 2005, *Amyloid*, 12:88-95), the definition of trimer, tetramer, and the like, as used herein, is according to SDS-PAGE analysis. To illustrate the differential binding capabilities of the antibodies herein, it has been found that certain antibodies will recognize one multi-dimensional conformation, for example, tetramers of ADDLs (U.S. Pat. No. 7,780,963, murine antibodies 2D6 and 4E2), while other antibodies recognize several multi-dimensional conformations, for example, trimers and tetramers of ADDLs (U.S. Pat. No. 7,780,963, murine antibodies 2A10, 2B4, 5F10, and 20C2 and humanized antibody 20C2). As such, the antibody of the present invention has oligomer-specific characteristics. In particular embodiments, a multi-dimensional conformation of an ADDL is associated with a specific polypeptide structure which results in a conformational epitope that is recognized by an antibody of the present invention. In other embodiments, an antibody of the invention specifically binds a multi-dimensional conformation ADDL having a size range of approximately a trimer or tetramer, which have molecular weights in excess of >50 kDa.

While antibodies of the present invention may have similar linear epitopes, such linear epitopes are not wholly indicative of the binding characteristics of these antibodies, i.e., ability to block ADDL binding to neurons, prevent tau phosphorylation and inhibit ADDL assembly, because, as is well-known to the skilled artisan, the linear epitope may only correspond to a portion of the antigen's epitope (see, for example, Breitling and Dübel, 1999, *Recombinant Antibodies*, John Wiley & Sons, Inc., NY, pg. 115). The antibodies of the present invention can be distinguished from those of the art as being capable of differentially recognizing multi-dimensional ADDLs and accordingly differentially blocking ADDL binding to neurons, differentially preventing tau phosphorylation and differentially inhibiting ADDL assembly.

An antibody, as used in accordance with the present invention includes, but is not be limited to, polyclonal or monoclonal antibodies, and chimeric, human (for example, isolated from B cells), humanized, neutralizing, bispecific or single chain antibodies thereof. In one embodiment, an antibody of the present invention is monoclonal. For the production of antibodies, various hosts including goats, rabbits, chickens, rats, mice, humans, and others, can be immunized by injection with synthetic or natural ADDLs. Methods for producing antibodies are well-known in the art. See, for example, Kohler and Milstein, 1975, *Nature* 256:495-497: Harlow and Lane, *Antibodies: A Laboratory Manual*, Cold Spring Harbor Laboratory, New York, 1988.

Depending on the host species, various adjuvants can be used to increase the immunological response. Adjuvants used in accordance with the present invention desirably augment the intrinsic response to ADDLs without causing conformational changes in the immunogen that affect the qualitative form of the response. Particularly suitable adjuvants include 3 De-O-acylated monophosphoryl lipid A (MPL™; RIBI ImmunoChem Research Inc., Hamilton, Mont.; see GB 2220211) and oil-in-water emulsions, such as squalene or peanut oil, optionally in combination with immune stimulants, such as monophosphoryl lipid A (see, Stoute, et al., 1997, *N. Engl. J. Med.*, 336:86-91), muramyl peptides (for example, N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'dipalmitoyl-sn-glycero-3-hydroxyphosphoryloxy)-ethylamine (E-PE), N-acetylglucsaminyl-N-acetyl-muramyl-L-Al-D-isoglu-L-Ala-dipalmitoxy propylamide (DTP-DPP)), or other bacterial cell wall components. Specific examples of oil-in-water emulsions include MF59 (WO 90/14837), containing 5% Squalene, 0.5% TWEEN™ 80, and 0.5% SPAN 85 (optionally containing various amounts of MTP-PE) formulated into submicron particles using a microfluidizer such as Model 110Y microfluidizer (Microfluidics, Newton, Mass.); SAF containing 10% Squalene, 0.4% TWEEN™ 80, 5% PLURONIC®-blocked polymer L121, and thr-MDP, either microfluidized into a submicron emulsion or vortexed to generate a larger particle size emulsion; and RIBI™ adjuvant system (RAS) (Ribi ImmunoChem, Hamilton, Mont.) containing 2% squalene, 0.2% TWEEN™ 80, and one or more bacterial cell wall components such as monophosphoryllipid A, trehalose dimycolate (TDM), and cell wall skeleton (CWS).

Another class of adjuvants is saponin adjuvants, such as STIMULON™ (QS-21, Aquila, Framingham, Mass.) or particles generated therefrom such as ISCOMs (immunostimulating complexes) and ISCOMATRIX® (CSL Ltd., Parkville, Australia). Other suitable adjuvants include Complete Freund's Adjuvant (CFA), Incomplete Freund's Adjuvant (IFA), mineral gels such as aluminum hydroxide, and surface-active substances such as lysolecithin, PLURONIC® polyols, polyanions, peptides, CpG (WO 98/40100), keyhole limpet hemocyanin, dinitrophenol, and cytokines such as interleukins (IL-1, IL-2, and IL-12), macrophage colony stimulating factor (M-CSF), and tumor necrosis factor (TNF). Among adjuvants used in humans, BCG (bacilli Calmette-Guerin) and *Corynebacterium parvum* are particularly suitable.

An antibody to a multi-dimensional conformation ADDL is generated by immunizing an animal with ADDLs. Generally, ADDLs can be generated synthetically or by recombinant fragment expression and purification. Synthetic ADDLs can be prepared as disclosed herein, or in accordance with the methods disclosed in U.S. Pat. Nos. 6,218,506 and 7,811,563, or in co-pending applications U.S. 2007/0218499, U.S. 2010/0143396, and U.S. 2010/0240868, all of which are incorporated herein by reference in their entirety. Further, ADDLs can be fused with another protein such as keyhole limpet hemocyanin to generate an antibody against the chimeric molecule. The ADDLs can be conformationally constrained to form an epitope useful as described herein and furthermore can be associated with a surface for example, physically attached or chemically bonded to a surface in such a manner so as to allow for the production of a conformation which is recognized by the antibodies of the present invention.

Monoclonal antibodies to multi-dimensional conformations of ADDLs can be prepared using any technique which provides for the production of antibody molecules by continuous cell lines in culture. These include, but are not limited to, the hybridoma technique, the human B-cell hybridoma technique, and the EBV-hybridoma technique (Kohler, et al., 1975, *Nature* 256:495-497; Kozbor, et al., 1985, *J. Immunol. Methods* 81:31-42; Cote, et al., 1983, *Proc. Natl. Acad. Sci.* 80:2026-2030; Cole, et al., 1984, *Mol. Cell Biol.* 62:109-120).

In particular embodiments, the antibodies of the present invention are humanized. Humanized or chimeric antibodies can be produced by splicing of mouse antibody genes to human antibody genes to obtain a molecule with appropriate antigen specificity and biological activity (see, Morrison, et al., 1984, *Proc. Natl. Acad. Sci.* 81, 6851-6855; Neuberger, et al., 1984, *Nature* 312:604-608; Takeda, et al., 1985, *Nature* 314:452-454; Queen, et al., 1989, *Proc. Natl. Acad. Sci. USA* 86:10029-10033; WO 90/07861). For example, a mouse antibody is expressed as the Fv or Fab fragment in a phage selection vector. The gene for the light chain (and in a parallel experiment, the gene for the heavy chain) is exchanged for a library of human antibody genes. Phage antibodies, which still bind the antigen, are then identified. This method, commonly known as chain shuffling, provided humanized antibodies that should bind the same epitope as the mouse antibody from which it descends (Jespers, et al., 1994, *Biotechnology NY* 12:899-903). As an alternative, chain shuffling can be performed at the protein level (see, Figini, et al., 1994, *J. Mol. Biol.* 239:68-78).

Human antibodies can also be obtained using phage-display methods. See, for example, WO 91/17271 and WO 92/01047. In these methods, libraries of phage are produced in which members display different antibodies on their outer surfaces. Antibodies are usually displayed as Fv or Fab fragments. Phage displaying antibodies with a desired specificity are selected by affinity enrichment to ADDLs. Human antibodies against ADDLs can also be produced from non-human transgenic mammals having transgenes encoding at least a segment of the human immunoglobulin locus and an inactivated endogenous immunoglobulin locus. See, for example, WO 93/12227 and WO 91/10741. Human antibodies can be selected by competitive binding experiments, or otherwise, to have the same epitope specificity as a particular mouse antibody. Such antibodies generally retain the useful functional properties of the mouse antibodies. Human polyclonal antibodies can also be provided in the form of serum from humans immunized with an immunogenic agent. Optionally, such polyclonal antibodies can be concentrated by affinity purification using ADDLs as an affinity reagent.

As exemplified herein, humanized antibodies can also be produced by veneering or resurfacing of murine antibodies. Veneering involves replacing only the surface fixed region amino acids in the mouse heavy and light variable regions with those of a homologous human antibody sequence. Replacing mouse surface amino acids with human residues in the same position from a homologous human sequence has been shown to reduce the immunogenicity of the mouse antibody while preserving its ligand binding. The replacement of exterior residues generally has little, or no, effect on the interior domains, or on the inter-domain contacts. See, for example, U.S. Pat. No. 6,797,492.

Human or humanized antibodies can be designed to have IgG, IgD, IgA, IgM or IgE constant regions, and any isotype, including IgG1, IgG2, IgG3 and IgG4. In particular embodiments, an antibody of the invention is IgG or IgM, or a combination thereof. In one specific embodiment the antibodies of the present invention are IgG2. Those of skill in the art would understand that other isoforms can be utilized herein. Exemplary sequences for these isoforms are given in SEQ ID NOS: 43-45. Other embodiments of the present invention embrace a constant region formed by selective incorporation of human IgG4 sequences into a standard human IgG2 constant region. An exemplary mutant IgG2 Fc is IgG2m4, set forth herein as SEQ ID NO: 46. Antibodies can be expressed as tetramers containing two light and two heavy chains, as separate heavy chains and light chains or as single chain antibodies in which heavy and light chain variable domains are linked through a spacer. Techniques for the production of single chain antibodies are well-known in the art.

Exemplary humanized antibodies produced by CDR grafting and veneering are disclosed in U.S. Pat. Nos. 7,780,963, 7,731,962, and 7,811,563.

Diabodies are also contemplated. A diabody refers to an engineered antibody construct prepared by isolating the binding domains (both heavy and light chain) of a binding antibody, and supplying a linking moiety which joins or operably links the heavy and light chains on the same polypeptide chain thereby preserving the binding function (see, Holliger, et al., 1993, *Proc. Natl. Acad. Sci. USA* 90:6444; Poljak, 1994, *Structure* 2:1121-1123). This forms, in essence, a radically abbreviated antibody, having only the variable domain necessary for binding the antigen. By using a linker that is too short to allow pairing between the two domains on the same chain, the domains are forced to pair with the complementary domains of another chain and create two antigen-binding sites. These dimeric antibody fragments, or diabodies, are bivalent and bispecific. The skilled artisan will appreciate that any method to generate diabodies can be used. Suitable methods are described by Holliger, et al., 1993, supra; Poljak, 1994, supra; Zhu, et al., 1996, *Biotechnology* 14:192-196, and U.S. Pat. No. 6,492,123, which are incorporated herein by reference in their entirety.

Fragments of an isolated antibody of the invention are also expressly encompassed by the present invention. Fragments are intended to include Fab fragments, F(ab')$_2$ fragments, F(ab') fragments, bispecific scFv fragments, Fv fragments and fragments produced by a Fab expression library, as well as peptide aptamers. For example, F(ab')$_2$ fragments are produced by pepsin digestion of the antibody molecule of the invention, whereas Fab fragments are generated by reducing the disulfide bridges of the F(ab')$_2$ fragments. Alternatively, Fab expression libraries can be constructed to allow rapid and easy identification of monoclonal Fab fragments with the desired specificity (see, Huse, et al., 1989, *Science*, 254:1275-1281). In particular embodiments, antibody fragments of the present invention are fragments of neutralizing antibodies which retain the variable region binding site thereof, i.e. antigen binding fragment. Exemplary are F(ab')$_2$ fragments, F(ab') fragments, and Fab fragments. See, generally, *Immunology: Basic Processes*, 1985, $2^{nd}$ edition, J. Bellanti (Ed.) pp. 95-97.

Peptide aptamers which differentially recognize multi-dimensional conformations of ADDLs can be rationally designed or screened for in a library of aptamers (for example, provided by Aptanomics SA, Lyon, France). In general, peptide aptamers are synthetic recognition molecules whose design is based on the structure of antibodies. Peptide aptamers consist of a variable peptide loop attached at both ends to a protein scaffold. This double structural constraint greatly increases the binding affinity of the peptide aptamer to levels comparable to that of an antibody (nanomolar range).

Exemplary nucleic acid sequences encoding heavy and light chain variable regions for use in producing antibody and antibody fragments of the present invention are disclosed herein in SEQ ID NOS: 14 and 16. As will be appreciated by the skilled artisan, the heavy chain variable regions disclosed herein, such as that shown in SEQ ID NO: 16, can be used in combination with any one of the light chain variable regions disclosed herein to generate antibodies with modified affinities, dissociation, epitopes, and the like.

Antibodies or antibody fragments of the present invention can have additional moieties attached thereto. For example, a microsphere or microparticle can be attached to the antibody or antibody fragment, as described in U.S. Pat. No. 4,493,825, the disclosure of which is incorporated herein by reference in its entirety.

Moreover, particular embodiment embrace antibody or antibody fragments which are mutated and selected for increased antigen affinity, neutralizing activity (i.e., the ability to block binding of ADDLs to neuronal cells or the ability to block ADDL assembly), or a modified dissociation constant. Mutator strains of *E. coli* (Low, et al., 1996, *J. Mol. Biol.*, 260:359-368), chain shuffling (Figini, et al., 1994, supra), and PCR mutagenesis are established methods for mutating nucleic acid molecules encoding antibodies. By way of illustration, increased affinity can be selected for by contacting a large number of phage antibodies with a low amount of biotinylated antigen so that the antibodies compete for binding. In this case, the number of antigen molecules should exceed the number of phage antibodies, but the concentration of antigen should be somewhat below the dissociation constant. Thus, predominantly mutated phage antibodies with increased affinity bind to the biotinylated antigen, while the larger part of the weaker affinity phage antibodies remains unbound. Streptavidin can then assist in the enrichment of the higher affinity, mutated phage antibodies from the mixture (Schier, et al., 1996, *J. Mol. Biol.* 255:28-43). Exemplary affinity-maturated light chain CDR3 amino acid sequences are disclosed herein (see Table 4), with particular embodiments embracing a light chain CDR3 amino acid sequence of SEQ ID NO: 3 and specific embodiments of SEQ ID NOS: 7-13. The present invention also embraces alternative variations for light chain CDR1 (SEQ ID NO: 53) and CDR2 (SEQ ID NO: 54).

For some therapeutic applications it may be desirable to reduce the dissociation of the antibody from the antigen. To achieve this, phage antibodies are bound to biotinylated antigen and an excess of unbiotinylated antigen is added. After a period of time, predominantly the phage antibodies with the lower dissociation constant can be harvested with streptavidin (Hawkins, et al., 1992, *J. Mol. Biol.* 226:889-96).

Various immunoassays including those disclosed herein can be used for screening to identify antibodies, or fragments thereof, having the desired specificity for multi-dimensional conformations of ADDLs. Numerous protocols for competitive binding (for example, ELISA), latex agglutination assays, immunoradiometric assays, kinetics (for example, Biacore™ analysis) using either polyclonal or monoclonal antibodies, or fragments thereof, are well-known in the art. Such immunoassays typically involve the measurement of complex formation between a specific antibody and its cognate antigen. A two-site, monoclonal-based immunoassay utilizing monoclonal antibodies reactive to two non-interfering epitopes is suitable, but a competitive binding assay can also be employed. Such assays can also be used in the detection of multi-dimensional conformations of ADDLs in a sample.

An antibody or antibody fragment can also be subjected to other biological activity assays, e.g., displacement of ADDL binding to neurons or cultured hippocampal cells or blockade of ADDL assembly, in order to evaluate neutralizing or pharmacological activity and potential efficacy as a prophylactic or therapeutic agent. Such assays are described herein and are well-known in the art.

Antibodies and fragments of antibodies can be produced and maintained as hybridomas or, alternatively, recombinantly produced in any well-established expression system including, but not limited to, *E. coli*, yeast (e.g., *Saccharomyces* spp. and *Pichia* spp.), baculovirus, mammalian cells (e.g., myeloma, CHO, COS), plants, or transgenic animals (Breitling and Dübel, 1999, *Recombinant Antibodies*, John Wiley & Sons, Inc., NY, pp. 119-132). Antibodies and fragments of antibodies can be isolated using any appropriate methods including, but not limited to, affinity chromatography, immunoglobulins-binding molecules (for example, proteins A, L, G or H), tags operatively linked to the antibody or antibody fragment (for example, His-tag, FLAG®-tag, Strep tag, c-myc tag) and the like. See, Breitling and Dübel, 1999 supra.

Antibodies and antibody fragments of the present invention have a variety of uses including, diagnosis of diseases associated with accumulation of ADDLs, blocking or inhibiting binding of ADDLs to neuronal cells, blocking ADDL assembly, prophylactically or therapeutically treating a disease associated with ADDLs, identifying therapeutic agents that prevent binding of ADDLs to neurons, and preventing the phosphorylation of tau protein at Ser202/Thr205.

Antibody and antibody fragments of the present invention are useful in a method for blocking or inhibiting binding of ADDLs to neuronal cells. This method of the invention is carried out by contacting a neuron, in vitro or in vivo, with an antibody or antibody fragment of the present invention so that binding of ADDLs to the neuron is blocked. In particular embodiments, an antibody or antibody fragment of the present invention achieves at least a 15%, 20%, 30%, 40%, 50%, 60%, 70%, 80%, 90%, 95%, or 97% decrease in the binding of ADDLs as compared to binding of ADDLs in the absence of the antibody or antibody fragment. The degree to which an antibody can block the binding of ADDLs to a neuron can be determined in accordance with the methods disclosed herein, i.e., immunocytochemistry, or cell-based alkaline phosphatase assay, or any other suitable assay. Antibodies particularly useful for decreasing binding of ADDLs to neuronal cells include the exemplary anti-ADDL antibodies shown in U.S. Pat. Nos. 7,731,962, 7,780,963, and 7,811,563, as well as derivatives and fragments thereof.

Antibody and antibody fragments of the present invention are further useful in a method for blocking or inhibiting assembly of ADDLs. This method involves contacting a sample containing amyloid β 1-42 peptides with an antibody or antibody fragment of the present invention so that ADDL assembly is inhibited. The degree to which an antibody can block the assembly of ADDLs can be determined in accordance with the methods disclosed herein, i.e., FRET or fluorescence polarization or any other suitable assay. Antibodies particularly useful for blocking the assembly of ADDLs include anti-ADDL antibodies having a CDR3 amino acid sequence set forth in SEQ ID NO: 10, as well as derivatives and fragments thereof.

Antibodies disclosed herein are also useful in methods for preventing the phosphorylation of tau protein at Ser202/Thr205. This method involves contacting a sample containing tau protein with an antibody or antibody fragment of the present invention so that binding of ADDLs to neurons is blocked thereby preventing phosphorylation of tau protein. The degree to which an antibody can prevent the phosphorylation of tau protein at Ser202/Thr205 can be determined in accordance with the methods disclosed herein or any other suitable assay.

Blocking or decreasing binding of ADDLs to neurons, inhibiting assembly of ADDLs, and preventing the phosphorylation of tau protein at Ser202/Thr205 all find application in methods of prophylactically or therapeutically treating a disease associated with the accumulation of ADDLs. Accordingly, the present invention also embraces the use of an antibody or antibody fragment herein to prevent or treat a disease associated with the accumulation of ADDLs (for example, Alzheimer's disease or similar memory-related disorders). Evidence in the art indicates that elevated levels of Aβ, but not necessarily aggregated plaque, cause Alzheimer's disease-associated dementia and subsequent tau abnormalities. Aβ-derived diffusible ligands are directly implicated in neurotoxicity associated with Alzheimer's disease. The art indicates that ADDLs are elevated in transgenic mice and Alzheimer's disease patients and modulate functional activity associated with mnemonic processes in animal models. Thus, removing this form of Aβ could provide relief from the neurotoxicity associated with Alzheimer's disease. As such, treatment with an antibody of the present invention that reduces central nervous system ADDL load could prove efficacious for the treatment of Alzheimer's disease. Patients amenable to treatment include individuals at risk of disease but not exhibiting symptoms, as well as patients presently exhibiting symptoms. In the case of Alzheimer's disease, virtually anyone is at risk of suffering from Alzheimer's disease if he or she lives long enough. Therefore, the antibody or antibody fragments of the present invention can be administered prophylactically to the general population without the need for any assessment of the risk of the subject patient. The present methods are especially useful for individuals who have a known genetic risk of Alzheimer's disease. Such individuals include those having relatives who have been diagnosed with the disease, and those whose risk is determined by analysis of genetic or biochemical markers. Genetic markers of risk for Alzheimer's disease include mutations in the APP gene, particularly mutations at position 717 and positions 670 and 671 referred to as the Hardy and Swedish mutations respectively. Other markers of risk are mutations in the presenilin genes, PS1 and PS2, and ApoE4, family history of Alzheimer's disease, hypercholesterolemia or atherosclerosis. Individuals presently suffering from Alzheimer's disease can be recognized from characteristic dementia, as well as the presence of risk factors described above. In addition, a number of diagnostic tests are available for identifying individuals who have Alzheimer's disease. These include measurement of CSF tau and Aβ1-42 levels. Individuals suffering from Alzheimer's disease can also be diagnosed by ADRDA criteria or the method disclosed herein.

In asymptomatic patients, treatment can begin at any age (for example, 10, 20, 30 years of age). Usually, however, it is not necessary to begin treatment until a patient reaches 40, 50, 60 or 70 years of age. Treatment typically entails multiple dosages over a period of time. Treatment can be monitored by assaying for the presence of ADDLs over time.

In therapeutic applications, a pharmaceutical composition or medicament containing an antibody or antibody fragment of the invention is administered to a patient suspected of, or already suffering from such a disease associated with the accumulation of ADDLs in an amount sufficient to cure, or at least partially arrest, the symptoms of the disease (biochemical, histologic and/or behavioral), including its complications and intermediate pathological phenotypes in development of the disease. In prophylactic applications, a pharmaceutical composition or medicament containing an antibody or antibody fragment of the invention is administered to a patient susceptible to, or otherwise at risk of, a disease associated with the accumulation of ADDLs in an amount sufficient to achieve passive immunity in the patient thereby eliminating or reducing the risk, lessening the severity, or delaying the onset of the disease, including biochemical, histologic and/or behavioral symptoms of the disease, its complications and intermediate pathological phenotypes present during development of the disease. In some methods, administration of agent reduces or eliminates myocognitive impairment in patients that have not yet developed characteristic Alzheimer's pathology. In particular embodiments, an effective amount of an antibody or antibody fragment of the invention is an amount which achieves at least a 15%, 20%, 30%, 40%, 50%, 60%, 70%, 80%, 90%, 95%, or 97% decrease in the binding of ADDLs to neurons in the patient as compared to binding of ADDLs in the absence of treatment. As such, impairment of long-term potentiation/memory formation is decreased.

Effective doses of the compositions of the present invention, for the treatment of the above described conditions vary depending upon many different factors, including means of administration, physiological state of the patient, whether the patient is human or an animal, other medications administered, and whether treatment is prophylactic or therapeutic. Usually, the patient is a human but nonhuman mammals such as dogs or transgenic mammals can also be treated.

Treatment dosages are generally titrated to optimize safety and efficacy. For passive immunization with an antibody or antibody fragment, dosage ranges from about 0.0001 to 100 mg/kg, and more usually 0.01 to 5 mg/kg, of the host body weight are suitable. For example, dosages can be 1 mg/kg body weight or 10 mg/kg body weight or within the range of 1-10 mg/kg. In some methods, two or more antibodies of the invention with different binding specificities are administered simultaneously, in which case the dosage of each antibody administered falls within the ranges indicated. Antibodies are usually administered on multiple occasions, wherein intervals between single dosages can be weekly, monthly or yearly. An exemplary treatment regime entails subcutaneous dosing, once biweekly or monthly. Intervals can also be irregular as indicated by measuring blood levels of antibody to ADDLs in the patient. In some methods, dosage is adjusted to achieve a plasma antibody concentration of 1-1000 mg/mL and in some methods 25-300 μg/mL. Alternatively, the antibody or antibody fragment can be administered as a sustained-release formulation, in which case less frequent administration is required. Dosage and frequency vary depending on the half-life of the antibody in the patient. In general, human and humanized antibodies have longer half-lives than chimeric antibodies and nonhuman antibodies. As indicated above, dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Antibody and antibody fragments of the present invention can be administered as a component of a pharmaceutical composition or medicament. Pharmaceutical compositions or medicaments generally contain the active therapeutic agent and a variety of other pharmaceutically acceptable components. See, *Remington: The Science and Practice of Pharmacy*, Alfonso R. Gennaro, editor, 20th ed. Lippincott Williams & Wilkins: Philadelphia, Pa., 2000. The preferred form depends on the intended mode of administration and therapeutic application. Pharmaceutical compositions can contain, depending on the formulation desired, pharmaceutically-acceptable, non-toxic carriers or diluents, which are defined as vehicles commonly used to formulate pharmaceutical compositions for animal or human administration. Diluents are selected so as not to affect the biological activity of the combination. Examples of such diluents are distilled water, physiological phosphate-buffered saline, Ringer's solutions, dextrose solution, and Hank's solution.

Pharmaceutical compositions can also contain large, slowly metabolized macromolecules such as proteins, polysaccharides such as chitosan, polylactic acids, polyglycolic acids and copolymers (such as latex-functionalized SEPHAROSE™, agarose, cellulose, and the like), polymeric amino acids, amino acid copolymers, and lipid aggregates (such as oil droplets or liposomes).

Administration of a pharmaceutical composition or medicament of the invention can be carried out in a variety of routes including, but not limited to, oral, topical, pulmonary, rectal, subcutaneous, intradermal, intranasal, intracranial, intramuscular, intraocular, or intrathecal or intra-articular injection, and the like. The most typical route of administration is intravenous followed by subcutaneous, although other routes can be equally effective. Intramuscular injection can also be performed in the arm or leg muscles. In some methods, agents are injected directly into a particular tissue where deposits have accumulated, for example, intracranial or intrathecal injection. In some embodiments, an antibody or antibody fragment is injected directly into the cranium or CSF. In other embodiments, antibody or antibody fragment is administered as a sustained-release composition or device, such as a MEDIPAD™ device.

For parenteral administration, antibody or antibody fragments of the invention can be administered as injectable dosages of a solution or suspension of the substance in a physiologically acceptable diluent with a pharmaceutical carrier that can be a sterile liquid such as water, oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are suitable liquid carriers, particularly for injectable solutions. Antibodies can be administered in the form of a depot injection or implant preparation which can be formulated in such a manner as to permit a sustained-release of the active ingredient.

An exemplary composition contains an isolated antibody, or antibody fragment thereof, of the present invention formulated as a sterile, clear liquid at a concentration of at least 10 mg/ml in isotonic buffered saline (10 mM histidine, 150 mM sodium chloride, 0.01% (w/v) POLYSORBATE 80, pH 6.0). An exemplary antibody formulation is filled as a single dose, 0.6 ml glass vials filled with 3.3 ml of solution per vial. Each vial is stopped with a TEFLON-coated stopper and sealed with an aluminum cap.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced delivery.

For suppositories, binders and carriers include, for example, polyalkylene glycols or triglycerides; such suppositories can be formed from mixtures containing the active ingredient in the range of 0.5% to 10%, or more desirably 1%-2%.

Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained-release formulations or powders and contain 10%-95% of active ingredient, or more suitably 25%-70%.

Topical application can result in transdermal or intradermal delivery. Topical administration can be facilitated by co-administration of the agent with cholera toxin or detoxified derivatives or subunits thereof or other similar bacterial toxins (see Glenn, et al. (1998) Nature 391:851). Co-administration can be achieved by using the components as a mixture or as linked molecules obtained by chemical crosslinking or expression as a fusion protein.

Alternatively, transdermal delivery can be achieved using a skin path or using transferosomes (Paul, et al., 1995, Eur. J. Immunol 25:3521-3524; Cevc, et al., 1998, Biochem. Biophys. Acta 1368:201-215).

An antibody or antibody fragment of the invention can optionally be administered in combination with other agents that are at least partly effective in treatment of amyloidogenic disease. For example, the present antibody can be administered with existing palliative treatments for Alzheimer's disease, such as acetylcholinesterase inhibitors such as ARICEPT™, EXELON™, and REMINYL™ and, the NMDA antagonist, NAMENDA™. In addition to these approved treatments, the present antibody can be used to provide synergistic/additive benefit for any of several approaches currently in development for the treatment of Alzheimer's disease, which include without limitation, inhibitors of Aβ production and aggregation.

Antibody and antibody fragments of the present invention also find application in the identification of therapeutic agents that prevent the binding of ADDLs to neurons (e.g., a hippocampal cell) thereby preventing downstream events attributed to ADDLs. Such an assay is carried out by contacting a neuron with ADDLs in the presence of an agent and using an antibody of antibody fragment of the invention to determine binding of the ADDLs to the neuron in the presence of the agent. As will be appreciated by the skilled artisan, an agent that blocks binding of ADDLs to a neuron will decrease the amount of ADDLs bound to the neuron as compared to a neuron which has not been contacted with the agent; an amount which is detectable in an immunoassay employing an antibody or antibody fragment of the present invention. Suitable immunoassays for detecting neuronal-bound ADDLs are disclosed herein.

Agents which can be screened using the method provided herein encompass numerous chemical classes, although typically they are organic molecules, preferably small organic compounds having a molecular weight of more than 100 and less than about 2,500 daltons. Agents encompass functional groups necessary for structural interaction with proteins, particularly hydrogen bonding, and typically include at least an amine, carbonyl, hydroxyl or carboxyl group, preferably at least two of the functional chemical groups. The agents often contain cyclical carbon or heterocyclic structures and/or aromatic or polyaromatic structures substituted with one or more of the above functional groups. Agents can also be found among biomolecules including peptides, antibodies, saccharides, fatty acids, steroids, purines, pyrimidines, derivatives, structural analogs or combinations thereof. Agents are obtained from a wide variety of sources including libraries of natural or synthetic compounds.

A variety of other reagents such as salts and neutral proteins can be included in the screening assays. Also, reagents that otherwise improve the efficiency of the assay, such as protease inhibitors, nuclease inhibitors, anti-microbial agents, and the like can be used. The mixture of components can be added in any order that provides for the requisite binding.

Agents identified by the screening assay of the present invention will be beneficial for the treatment of amyloidogenic diseases and/or tauopathies. In addition, it is contemplated that the experimental systems used to exemplify these concepts represent research tools for the evaluation, identification and screening of novel drug targets associated with amyloid beta induction of tau phosphorylation.

The present invention also provides methods for detecting ADDLs and diagnosing a disease associated with accumulation of ADDLs using an antibody or antibody fragment herein. A disease associated with accumulation of ADDLs is intended to include any disease wherein the accumulation of ADDLs results in physiological impairment of long-term potentiation/memory formation. Diseases of this type include, but are not limited to, Alzheimer's disease and similar memory-related disorders.

In accordance with these methods, a sample from a patient is contacted with an antibody or antibody fragment of the invention and binding of the antibody or antibody fragment to the sample is indicative of the presence of ADDLs in the sample. As used in the context of the present invention, a sample is intended to mean any bodily fluid or tissue which is amenable to analysis using immunoassays. Suitable samples which can be analyzed in accordance with the methods of the invention include, but are not limited to, biopsy samples and fluid samples of the brain from a patient (for example, a mammal such as a human). For in vitro purposes (for example, in assays monitoring oligomer formation), a sample can be a neuronal cell line or tissue sample. For diagnostic purposes, it is contemplated that the sample can be from an individual suspected of having a disease associated with accumulation of ADDLs or from an individual at risk of having a disease associated with accumulation of ADDLs, for example, an individual with a family history which predisposes the individual to a disease associated with accumulation of ADDLs.

Detection of binding of the antibody or antibody fragment to ADDLs in the sample can be carried out using any standard immunoassay (for example, as disclosed herein), or alternatively when the antibody fragment is, for example, a peptide aptamer, binding can be directly detected by, for example, a detectable marker protein (for example, β-galactosidase, GFP or luciferase) fused to the aptamer. Subsequently, the presence or absence of the ADDL-antibody complex is correlated with the presence or absence, respectively, of ADDLs in the sample and therefore the presence or absence, respectively, of a disease associated with accumulation of ADDLs. It is contemplated that one or more antibodies or antibody fragments of the present invention can be used in conjunction with current non-invasive immuno-based imaging techniques to greatly enhance detection and early diagnosis of a disease associated with accumulation of ADDLs.

To facilitate diagnosis, the present invention also pertains to a kit containing an antibody or antibody fragment herein. The kit includes a container holding one or more antibodies or antibody fragments which recognize multi-dimensional conformation of ADDLs and instructions for using the antibody for the purpose of binding to ADDLs to form an antibody-antigen complex and detecting the formation of the antibody-antigen complex such that the presence or absence of the antibody-antigen complex correlates with presence or absence of ADDLs in the sample. Examples of containers include multiwell plates which allow simultaneous detection of ADDLs in multiple samples.

All references cited herein are incorporated herein by reference in their entirety.

The invention is described in greater detail by the following non-limiting examples.

EXAMPLES

The following abbreviations are used herein: Ab: antibody; Aβ: amyloid beta protein; AD: Alzheimer's disease; ADDL: amyloid-β (Aβ)-derived diffusible ligand; Ag: antigen; APP: amyloid precursor protein; bADDLs: biotinylated ADDLs; CSF: cerebrospinal fluid; DMSO: dimethyl sulfoxide; hAPP: human amyloid precursor protein; HAT medium: hypoxanthine-aminopterin-thymidine medium; HFIP: hexafluoro-2-propanol; IV: intravenous; LB agar: lysogeny broth agar; SC: subcutaneous; PBS: phosphate buffered saline; TEA: Triethylamine.

Example 1

General Materials and Methods

A. Generation of ADDL Monoclonal Antibodies

Soluble Aβ oligomers, a species of which is referred to herein as "synthetic" ADDLs, were mixed 1:1 with complete Freund's adjuvant (first and second vaccination) or incomplete Freund's adjuvant (all subsequent vaccinations) and were given by subcutaneous (first two vaccinations) or intraperitoneal injection into three mice in a total volume of 1 mL/mouse. Each injection consisted of purified ADDLs equivalent to 194±25 µg total protein. Mice were injected approximately every three weeks. After six injections, one mouse died and its spleen was frozen. The spleen from the mouse with the highest titer serum was then fused with SP2/0 myeloma cells in the presence of polyethylene glycol and plated out into six 96-well plates. The cells were cultured at 37° C. with 5% $CO_2$ for 10 days in 200 µL of hypoxanthine-aminopterin-thymidine (HAT) selection medium, which is composed of an enriched synthetic medium, such as Iscove's Modified Dulbecco's Medium (IMDM), (Sigma-Aldrich, St. Louis, Mo.), supplemented with 10% fetal bovine serum (FBS), 1 µg/mL HYBRI-MAX® (azaserine-hypoxanthine; Sigma-Aldrich, MO), and 30% conditioned media collected from SP2/0 cell culture. The cultures were fed once with IMDM (Sigma-Aldrich, St. Louis, Mo.) supplemented with 10% FBS on day 10, and the culture supernatants were removed on day 14 to screen for positive wells in ELISA. The positive cultures were further cloned by limiting dilutions with probability of 0.3 cells per well. The positive clones were confirmed in ELISA and further expanded. Monoclonal antibodies were then produced and purified for use (QED Bioscience, San Diego, Calif.).

B. Preparation of ADDLs and bADDLs

ADDLs were prepared using previously described methods (Hepler, et al., 2006, *Biochemistry*, 45: 15157-15167; Shughrue, et al., 2010, *Neurobiol. Aging*, 31: 189-202). Briefly, synthetic Aβ1-42 peptide (American Peptide, Sunnyvale, Calif.) was dissolved in hexafluoro-2-propanol (HFIP) at a concentration of 10 mg/ml, and incubated at room temperature (RT) for one hour. The peptide solution was dispensed into 50 µl aliquots in polypropylene 1.5 ml microcentrifuge tubes. The HFIP was removed using a SpeedVac® (Thermo-Fisher Scientific, Waltham, Mass.), and the resulting peptide films were stored desiccated at −70° C. until needed. A 0.5 mg dried HFIP film was dissolved in 22 µl of anhydrous dimethyl sulfoxide (DMSO) with agitation for 10 minutes on a vortex mixer. Subsequently, 1 ml of cold Ham's F12 media without phenol red (United Biosource, San Francisco, Calif.) was added rapidly to the DMSO/peptide mixture. The tube was capped, inverted to insure complete mixing and incubated overnight at 4° C. The next morning the samples were centrifuged for ten minutes at 12,000×g in a Beckman microcentrifuge (Beckman Coulter, Brea, Calif.) operated at 2-8° C. The supernatant was collected and filtered through ym 50 (50,000 kDa molecular cutoff) Centricon® centrifugal filter (Millipore, Billerica, Mass.) to enrich the oligomeric species. Biotinylated ADDLs (bADDLs) were prepared using the same methods, but starting with N-terminal biotinylated Aβ1-42 peptide (American Peptide, Sunnyvale, Calif.).

C. Monomer and Fibril Preparations

To generate monomer preparations, RT Aβ1-40 or Aβ1-42 peptide film was dissolved in 2 mL of 25 mM borate buffer (pH 8.5) per mg of peptide, divided into aliquots, and frozen at −70° C. until used. The fibril preparations were made by adding 2 mL of 10 mM hydrochloric acid per mg of Aβ1-42 peptide film. The solution was mixed on a vortex mixer at the lowest possible speed for five to ten minutes and the resulting preparation was stored at 37° C. for 18 to 24 hours before use.

D. Primary Neurons

Primary neuronal cultures were prepared from rat hippocampal and/or cortical tissues purchased from BrainBits (Springfield, Ill.). After dissociation, cells were plated at a 35,000 cells/well in 96-well plates pre-coated with laminin and poly-D-lysine (Corning Life Sciences, Lowell, Mass.). Cells were maintained at 37° C. with 5% $CO_2$ in media (Neurobasal supplemented with 2% B27, 1% L-glutamine, and 1% pen/strep; Invitrogen, Carlsbad, Calif.) for two-three weeks and then used for binding studies.

E. Cell-Based ADDL Binding Assay

To measure the effect of anti-ADDL antibodies on blocking ADDL binding, anti-ADDL antibodies were mixed with 500 nM bADDLs, with the final antibody concentrations ranging from 1.8 nM to 450 nM. As a control, the same concentration of heat-denatured antibody (98° C. for 30 minutes) was mixed with bADDLs. The antibody-bADDL mixtures were incubated in siliconized microcentrifuge tubes (Fischer Scientific, Pittsburgh, Pa.) at 37° C. for one hour with constant end-to-end rotation at a low speed. The mixtures were then applied to primary hippocampal and/or cortical cultures and incubated at 37° C. for one hour. The incubation was terminated by removing the culture medium. Cells were subjected to fixation and post-fixation treatments as described above. Cells were then incubated with streptavidin conjugated with alkaline phosphate (AP) at 4° C. overnight, washed five times with PBS and reacted with the Tropix® CDP®-Star chemiluminescent substrate (Life Technologies™, Carlsbad, Calif.) at room temperature for 30 minutes. The bADDL binding intensity was measured and recorded with an EnVision® microplate reader (PerkinElmer, Waltham, Mass.).

F. ELISA

Biotinylated ADDLs (bADDLs) or monomer Aβ1-40 or Aβ1-42 was added to a high-capacity streptavidin-coated plate (Sigma-Aldrich, St. Louis, Mo.) with 100 μL per well of coating reagent in PBS at 1 μM and incubated for two hours at room temperature. The plates were washed in PBS with 0.05% Tween (six times) and then PBS alone (three times) prior to blocking wells with 5% non-fat dry milk in PBS for one hour at room temperature. The wells were then washed and a serial dilution of antibody samples added to the plates and allowed to bind for two hours at room temperature. After incubation and washing, the antibody binding was detected with a goat anti-human IgG-Fc secondary antibody conjugated to horse radish peroxidase (HRP) (1:1,000; one hour at room temperature). The HRP label was visualized with tetramethyl benzidine (Virolabs, Chantilly, Va.) as a substrate and read at 450 nm on a microplate reader.

Example 2

Selection of Anti-ADDL Antibodies a. Panning Humanized Antibody Library

An affinity mature library of a humanized anti-ADDL antibody, h3B3, (See, U.S. 2006/0228349 and U.S. 2008/0175835) was constructed in which part of the light chain CDR3 amino acid sequences were subject to random mutagenesis. To cover the entire CDR3 region, two sub-libraries were built. One library was composed of the parental heavy chain variable region and mutated amino acids in the left half of the light chain CDR3 and the other in the right half of the light chain CDR3. A similar strategy was used for heavy chain CDRs random mutagenesis with three sub-libraries.

Humanized 3B3 (h3B3) was subject to affinity maturation using methods known in the art. The h3B3 variable regions were cloned in a Fab display vector (pFab3D). In this vector, the variable regions for heavy and light chains were in-frame inserted to match the CH1 domain of the constant region and the kappa constant region, respectively. In Fab3D, myc epitope and six consecutive histidine amino acids follow the CH1 sequence, which is then linked to the phage pIII protein for display. All positions in the heavy and light chain CDR3s were randomly mutagenized using degenerate oligonucleotide sequences built in the PCR primers. To accommodate the physical size, the sub-libraries were constructed with each focusing on 5-6 amino acids. The vector DNA of human 3B3 (H3B3) was used as template DNA to amplify both heavy and light chains with the mutated PCR primers (Table 1). After PCR amplification, the synthesized DNA fragments were run on a 1.3% agarose gel, the primers removed and the variable fragments digested with restriction enzymes: BsiWI and XbaI cloning sites for light chain variable cloning, XhoI and ApaI for heavy chain variable cloning.

TABLE 1

| 3B3 Affinity Maturation Library | Forward PCR Primer | Reverse PCR Primers |
|---|---|---|
| Light Chain Libraries | SEQ ID NO: 22 | SEQ ID NO: 23 SEQ ID NO: 24 |
| Heavy Chain Libraries | SEQ ID NO: 25 | SEQ ID NO: 26 SEQ ID NO: 27 |

To construct an affinity maturation library in pFab3D phage display vector, pFab3D-3B3 DNA was digested with the same pair of the restriction enzymes, purified and the PCR fragments for heavy or light chain variables ligated with T4 ligase (Invitrogen) overnight at 16° C. The ligation products were then transfected into *E. coli* TG1 electroporation-competent cells (Stratagene, Agilent Technologies, Santa Clara, Calif.) and aliquots of the bacterial culture plated on LB agar-carbenicillin (50 μg/mL) plates to titer library size. The remaining cultures were either plated on a large plate with carbenicillin and incubated at 30° C. overnight for *E. coli* library stock or infected with helper phage M13K07 (Invitrogen, Carlsbad, Calif., $10^{11}$ pfu/mL) by incubating at room temperature and 37° C. for ten minutes. Then 2YT medium with carbenicillin (50 μg/mL) was added and incubated at 37°

C. for one hour with shaking. Kanamycin (70 µg/ml) was then added and the cultures grown overnight at 30° C. with shaking. The phage culture supernatant was tittered and concentrated by precipitation with 20% (v/v) PEG (polyethleneglycol)/NaCl, resuspended in PBS, sterilized with a 0.22 µm filter, and aliquots made for phage library panning.

Phage library panning was then conducted as summarized in Table 2.

TABLE 2

| | Panning Rounds | | | |
|---|---|---|---|---|
| | Round 1 | Round 2 | Round 3 | Round 4 |
| Antigen concentration | 180 nM | 60 nM | 20 nM | 10 nM |

Input phages from the Fab display phage libraries (100 µl, about $10^{11-12}$ pfu) were blocked with 900 µL of blocking solution (3% non-fat dry milk in PBS) to reduce nonspecific binding to the phage surface. Streptavidin-coated beads were prepared by collecting 200 µL of the bead suspension in a magnetic separator and removing supernatants. The beads were then suspended in 1 mL of blocking solution and put on a rotary mixer for 30 minutes. To remove non-specific streptavidin binding phage, the blocked phage library was mixed with the blocked streptavidin-coated beads and placed on a rotary mixer for thirty minutes. Phage suspensions from the de-selection process were transferred to a new tube and 200 µL of antigen, 10% bADDL was added and incubated for two hours for antibody and antigen binding. After the incubation, the mixture was added into the blocked Streptavidin-coated beads and incubated on a rotary mixer for one hour to capture the Ab/Ag complex on streptavidin beads. The beads with captured 10% bADDL/phage complexes were washed five times with PBS/0.05% Tween 20 and then twice with PBS alone. The bound phages were eluted from the bADDL with 200 µL of 100 mM TEA (Sigma Aldrich, St. Louis, Mo.) and incubated for twenty minutes. The eluted phage were then transferred to a 50 mL tube, neutralized with 100 µL of IM Tris-HCl, pH7.5, and added to 10 mL of E. coli TG1 cells with an OD 600 nm between 0.6-0.8. After incubation at 37° C. with shaking for one hour, culture aliquots were plated on LB agar-carbenicillin (50 µg/mL) plates to titer the output phage number, and the remaining bacteria centrifuged and suspended with 500 µl 2×YT medium (Teknova, Hollister, Calif., plated on bioassay YT agar plates (Teknova, Hollister, Calif.) containing 100 µg/ml ampicillin and 1% glucose. The bioassay plates were grown overnight at 30° C.

After each round of panning, single colonies were randomly picked to produce phage in 96-well plates. The procedures for phage preparation in 96-well plate were similar to that described above except no phage precipitation step was used. Culture plates containing colonies growing in 120 µL of 2×TY medium with 100 µg/ml ampicillin and 0.1% glucose were incubated overnight in a HiGro® shaker (Genomic Solutions, Ann Arbor, Mich.) at 30° C. with shaking at 450 rpm. The phage supernatants (about 100 µL) were directly used for analysis in the ADDL binding ELISA described above. One difference is that the binding of phage to ADDLs was detected with an anti-M13-antibody conjugated to HRP (Amersham Bioscience, GE Healthcare, Waukesha, Wis.).

Example 3

Identification of Anti-ADDL Antibodies

From the light chain affinity maturation effort, a panel of seven clones showed strong binding activities to ADDLs when compared with h3B3 in a phage/Fab ELISA (data not shown). The seven clones were selected for conversion to IgGs and the monoclonal antibodies produced and purified for further characterization.

A. Anti-ADDL Antibody Selection

Following the library panning and screening described in Example 2, seven leading Fab clones (Tables 3-5) were selected for IgG conversion. Table 3 shows the amino acid similarity for the clones selected from the light chain affinity maturation library relative to parental antibody, h3B3. Table 4A summarizes the number of amino acid differences in the CDR3 of the light chain of the selected clones from the CDR3 of the light chain for the parental antibody, h3B3. Table 4B summarizes the number of amino acid differences in the CDR1 of the light chain of the selected clones from the CDR3 of the light chain for the parental antibody, 19.3. Table 4C summarizes the number of amino acid differences in the CDR2 of the light chain of the selected clones from the CDR3 of the light chain for the parental antibody, 19.3. Table 5 is an alignment of a portion (positions 21-117) of the light chain variable regions for the selected clones and the parental antibody, h3B3. CDR3 of each clone is shown in bold.

TABLE 3

| Antibody | 11.4 | 17.1 | 14.2 | 13.1 | 19.3 | 7.2 | 9.2 | h3B3-humanized LC |
|---|---|---|---|---|---|---|---|---|
| 11.4 | | 98 | 98 | 96 | 96 | 96 | 97 | 97 |
| 17.1 | | | 98 | 96 | 97 | 96 | 97 | 97 |
| 14.2 | | | | 96 | 97 | 98 | 98 | 98 |
| 13.1 | | | | | 97 | 97 | 97 | 96 |
| 19.3 | | | | | | 96 | 97 | 96 |
| 7.2 | | | | | | | 98 | 97 |
| 9.2 | | | | | | | | 97 |

TABLE 4A

| Antibody | LC-CDR3 sequences | Number of Amino Acid Differences from h3B3 |
|---|---|---|
| h3B3 (parental) | FQGSHVPPT (SEQ ID NO: 28) | 0 |
| 19.3 | FQGSRLGPS (SEQ ID NO: 10) | 4 |
| 17.1 | FQGSRVPAS (SEQ ID NO: 7) | 3 |
| 14.2 | FQGSRVPPG (SEQ ID NO: 8) | 2 |
| 13.1 | FQGSKAHPS (SEQ ID NO: 9) | 4 |
| 7.2 | FQGSYAPPG (SEQ ID NO: 11) | 3 |
| 9.2 | FQGSRAPPF (SEQ ID NO: 12) | 3 |
| 11.4 | FQGSRVPVR (SEQ ID NO: 13) | 3 |

TABLE 4B

| Antibody | LC-CDR1 sequences | Number of Amino Acid Differences from 19.3 (parental) |
|---|---|---|
| 19.3 (parental) | RSSQSIVHSNGNTYLE (SEQ ID NO: 1) | 0 |

TABLE 4B -continued

| Antibody | LC-CDR1 sequences | Number of Amino Acid Differences from 19.3 (parental) |
|---|---|---|
| 19.3 N33S | RSSQSIVHSSGNTYLE (SEQ ID NO: 55) | 1 |
| 19.3 N33T | RSSQSIVHSTGNTYLE (SEQ ID NO: 56) | 1 |
| 19.3 N33A | RSSQSIVHSAGNTYLE (SEQ ID NO: 57) | 1 |
| 19.3 N33E | RSSQSIVHSEGNTYLE (SEQ ID NO: 67) | 1 |
| 19.3 N33D | RSSQSIVHSDGNTYLE (SEQ ID NO: 68) | 1 |
| 19.3 N33S-N35Q | RSSQSIVHSSGQTYLE (SEQ ID NO: 59) | 2 |
| 19.3 N33S-N35S | RSSQSIVHSSGSTYLE (SEQ ID NO: 60) | 2 |
| 19.3 N33S-N35T | RSSQSIVHSSGTTYLE (SEQ ID NO: 61) | 2 |
| 19.3 N33S-N35A | RSSQSIVHSSGATYLE (SEQ ID NO: 62) | 2 |

TABLE 4C

| Antibody | LC-CDR2 sequences | Number of Amino Acid Differences from 19.3 (parental) |
|---|---|---|
| 19.3 (parental) | KASNRFS (SEQ ID NO: 2) | 0 |
| 19.3 N58Q | KASQRFS (SEQ ID NO: 63) | 1 |
| 19.3 N58S | KASSRFS (SEQ ID NO: 64) | 1 |
| 19.3 N58T | KASTRFS (SEQ ID NO: 65) | 1 |
| 19.3 N58A | KASARFS (SEQ ID NO: 66) | 1 |

TABLE 5

17.1
PASISCRSSQSIVHSNGNTYLEWYLQKPGQSPQLLIYKASNRFSGVPDRFSGSGSGTDFTLKISRVE
AEDVGVYYCFQGSRVPASFGQGTKLEIK (SEQ ID NO: 33)

14.2
PASISCRSSQSIVHSNGNTYLEWYLQKPGQSPQLLIYKASNRFSGVPDRFSGSGSGTDFTLKISRVE
AEDVGVYYCFQGSRVPPGFGQGTKLEIK (SEQ ID NO: 34)

13.1
PASISCRSSQSIVHSNGNTYLEWYLQKPGQSPQLLIYKASNRFSGVPDRFSGSGSGTDFILKISRVE
AEDVGVYYCFQGSKAHPSFGQGTKLEIK (SEQ ID NO: 35)

19.3
PASISCRSSQSIVHSNGNTYLEWYLQKPGQSPQLLIYKASNRFSGVPDRFSGSGSGTDFTLKISRVE
AEDVGVYYCFQGSRLGPSFGQGTKLEIK (SEQ ID NO: 36)

7.2
PASISCRSSQSIVHSNGNTYLEWYLQKPGQSPQLLIYKASNRFSGVPDRFSGSGSGTDFTLKISRVE
AEDVGVYYCFQGSYAPPGFGQGTKLEIK (SEQ ID NO: 37)

9.2
PASISCRSSQSIVHSNGNTYLEWYLQKPGQSPQLLIYKASNRFSGVPDRFSGSGSGTDFTLKISRVE
AEDVGVYYCFQGSRAPPFFGQGTKLEIK (SEQ ID NO: 38)

11.4
PASISCRSSQSIVHSNGNTYLEWYLQKPGQSPQLLIYKASNRFSGVPDRFSGSGSGTDFTLKISRVE
AEDVGVYYCFQGSRVPVRFGQGTKLEIK (SEQ ID NO: 39)

h3B3
PASISCRSSQSIVHSNGNTYLEWYLQKPGQSPQLLIYKASNRFSGVPDRFSGSGSGTDFTLKISRVE
AEDVGVYYCFQGSHVPPTFGQGTKLEIK (SEQ ID NO: 40)

B. IgG Conversion

The converted IgGs can be expressed using plasmid based vectors. The expression vectors were built such that they contain all the necessary components except the variable regions. In the basic vectors, the expression of both light and heavy chains was driven by human CMV promoter and bovine growth hormone polyadenylation signal. For the seven clones selected for IgG conversion, the heavy chain variable region was in-frame fused with a human IgG2 heavy chain constant region (SEQ ID NOS: 20 and 21), while the light chain variable region was in-frame fused with the kappa light chain constant region (SEQ ID NOS: 18 and 19). The heavy (SEQ ID NOS: 29 and 30) and light (SEQ ID NOS: 31 and 32) chain leader sequences, which mediate the secretion of the antibodies into the culture media, were also in-frame fused with the variable regions accordingly. For the heavy chain expression vectors, the constant region can be selected from a different subclass isotype, e.g., IgG1 or IgG2. Between the leader sequence and the constant region, the intergenic sequences contains cloning sequences for seamless in-frame fusion of the incoming variable region with the leader sequence at its 5'-end and the constant region at its 3'-end using In-Fusion cloning strategy (Clontech, Mountain View, Calif.). The In-Fusion™ Dry-Down PCR Cloning Kits (Clontech, Mountain View, Calif.) was used for PCR amplification of the variable regions. The dry-down cloning kit contains all the necessary components for PCR reaction. PCR primers and template DNAs were added. The expression vectors carry oriP from the EBV viral genome. The oriP/EBNA1 pair is often used to prolong the presence of the expression vector inside the transfected cells and widely used for the extension of the expression duration (Lindner, et al., 2007, *Plasmid* 58:1-12) for prolonged expression in 293EBNA cells, bacterial sequences for a kanamycin selection marker, and a replication origin in *E. coli*. When the variable regions were inserted, the IgGs were directly expressed in mammalian cells. All heavy chain variable regions herein were cloned into an IgG1 expression vector (pV1JNSA-BF-HCG1) and the light chain variable regions were cloned into a matching kappa or lambda expression vector (pV1JNSA-GS-FB-LCK).

C. Antibody Cloning

The cloning procedure for the resulting antibody expression vectors was as follows. The variable regions were PCR amplified in which the PCR reactions were carried out in a volume of 25 µL containing high fidelity PCR master mix, template volume 1 µL and forward and reverse primers: 1 µL each. PCR conditions: 1 cycle of 94° C., 2 minutes; 25 cycles of 94° C., 1.5 minutes; 60° C., 1.5 minutes; 72° C., 1.5 minutes and 72° C., 7 minutes; 4° C. until removed. The PCR products were then digested with DpnI and purified with QIAquick plate kit (Qiagen, Venlo, The Netherlands). 100 ng of the corresponding previously linearized heavy chain or light chain vectors annealed to 10 ng of the PCR fragment with an In-Fusion reaction (IN-Fusion Dry-Down Cloning Kit, Clontech, Mountain View, Calif.). The reaction mixture was transformed to XL2 Blue MRF' competent cells and plated overnight on Agar plates containing 50 µg/mL kanamycin. Light chain constructs were digested with HindIII+ NotI and heavy chain constructs were digested with AspI+ HindIII to check structure by restriction analysis. The DNA sequences for all the clones were confirmed by sequencing.

D. Antibody Expression in Mammalian Cells and Purification

Sequencing confirmed constructs of light chain and heavy chain DNA were transfected in 293 Freestyle cells (Invitrogen, Carlsbad, Calif.). The 293 Freestyle cells were transfected using 293 Transfectin (Invitrogen, Carlsbad, Calif.). EBNA monolayer cells were transfected using PEI based transfection reagents. Transfected cells were incubated at 37° C./5% $CO_2$ for seven days in Opti-MEM serum free medium (Invitrogen, Carlsbad, Calif.). The medium was collected, spun down, filtered through 0.22 µm filtration system (Millipore, Billerica, Mass.), and then concentrated by a Centricon® centrifuge filter (Millipore, Billerica, Mass.). Concentrated medium were mixed 1:1 with binding buffer (Pierce, Thermo Fisher Scientific, Rockford, Ill.), and then was loaded onto pre-equilibrated protein A/G column (Pierce, Thermo Fisher Scientific, Rockford, Ill.) or HI trap rProtein A FF from GE Healthcare, Waukesha, Wis. The loaded column was washed with binding buffer and eluted with elution buffer (Pierce, Thermo Fisher Scientific, Rockford, Ill.). Eluted antibody was neutralized immediately and dialyzed against buffer PBS for overnight. Dialyzed antibody was concentrated with an Amicon centrifuge filter (Pierce, Thermo Fisher Scientific, Rockford, Ill.) and protein concentration was determined by $OD_{280\ nm}$ with the extinct coefficient of 1.34 mg/mL. Purified antibody was analyzed using SDS-PAGE (Invitrogen, Carlsbad, Calif.), or protein labchip (Caliper LifeSciences, Hopkinton, Mass.). SDS-PAGE was run under non-reduced conditions.

The mutagenesis of the asparagine at position 33 (N33) of the light chain CDR1 for the antibody 19.3 into N33S (SEQ ID NO: 55), N33T (SEQ ID NO: 56), N33E (SEQ ID NO: 67), or N33D (SEQ ID NO: 68) was carried out by site directed mutagenesis from the WT expression vector of pV1JASN-GS-19.3-LCK using QuikChange II XL Site-Directed Mutagenesis Kit (Agilent Technologies, La Jolla, Calif.). The codon AAT for N was mutated to AGT for S in 19.3S33 (SEQ ID NO: 55), ACT for T in 19.3T33 (SEQ ID NO: 56), GAA for E in 19.3E33 (SEQ ID NO: 67), or GAT for D in 19.3D33 (SEQ ID NO: 68), and the new condons in that position were confirmed by DNA sequencing. To generate full-length IgG antibodies for these mutants, the respective light chain plasmids were paired with the cognate heavy chain plasmid, pV1JNSA-19.3-HCG2, for transient transfection in 293 FreeStyle cells (Invitrogen, Carlsbad, Calif.). The expression and purification methods were described above in this example. Aliquots of purified mutant antibodies along with the 19.3 parental antibody (SEQ ID NO: 1) were incubated under various conditions at 4° C., 25° C. or 40° C. for a month before being subjected to the ELISA analysis shown in FIGS. 4A-4C.

Example 4

Characterization of Anti-ADDL Antibodies

The selected anti-ADDL antibodies, i.e. those derived from the parental antibody, h3B3, where first assessed in a three-pronged Aβ ELISA to evaluate binding of the antibody to monomer Aβ, ADDLs, and fibrillar Aβ. As shown in FIG. 1, with the exception of antibody 9.2, all of the anti-ADDL antibodies showed preferential binding to ADDLs relative to h3B3, selective (Comp 1 and 3: bind only ADDLs), non-selective (Comp 2: bind all forms of Aβ evaluated) comparators, and a control (no antibody). Antibody 9.2 showed low binding to all forms of Aβ, which suggested that its binding affinity was adversely affected during IgG conversion and/or antibody production. A full titration curve (FIG. 2) was generated for each antibody and h3B3 to determine their binding affinity for ADDLs, as compared with monomer Aβ. Notwithstanding that six of the seven affinity matured antibodies showed preferential binding to ADDLs, Applicants have previously shown that some anti-ADDL antibodies having preferential binding to ADDLs are not able to prevent ADDL binding to primary hippocampal neurons (Shughrue, et al., 2010, *Neurobiol. Aging,* 31: 189-202, FIG. 1).

In that preferential binding to ADDLs alone may not be an accurate predictor of effectiveness, it would be desirable to identify anti-ADDL antibodies that also block ADDL binding to neurons, which can be evaluated in a cell-based binding assay as follows. Antibodies were pre-incubated with ADDLs and then added to primary hippocampal cultures to assess their blockade of ADDL binding. The results of this study showed that the anti-ADDL antibodies herein, specifically antibody 19.3, dramatically reduced ADDL binding to neurons (FIG. 3). However, a marked reduction in antibody activity in this assay was observed when the antibodies were heat-denatured (FIG. 3).

Determination of EC50. High protein binding plates (Costar, Corning, Lowell, Mass.), were coated with target ligand in PBS overnight at 4° C. The concentration of coating protein was 100 pmol/well for Aβ40 (American Peptide, Sunnyvale, Calif.) and 50 pmol/well for ADDLs. ADDLs were generated as described in Example 1B. Next day, plates were washed five times with PBS+0.05% Tween-20 (Sigma Aldrich, St. Louis, Mo.) and blocked overnight with Casein blocking buffer (ThermoScientific, Waltham, Mass.) and 0.05% Tween-20. Three representative antibodies, 19.3 (Fig. A), 19.3S33 (FIG. 4B), and 19.3T33 (FIG. 4C), generated as described in Example 3, were tested at 15 µg/m to 0 µg/m in a 12-point three-fold dilution series. After 2 hours at room temperature incubation, the plates were washed and alkaline phosphatase conjugated anti-human IgG (ThermoScientific, Waltham, Mass.) was added at 0.08 µg/ml. After 45 minutes at room temperature incubation, the plates were washed and Tropix® CDP®-Star chemiluminescent substrate (Life Technologies™, Carlsbad, Calif.) was added. Luminescence was detected after 30 minutes on an EnVision® microplate reader (PerkinElmer, Waltham, Mass.). Curve fits were completed using GraphPad Prism (GraphPad Software, Inc., San Diego, Calif.) software.

Example 5

In Vitro FcRn Binding of Anti-ADDL Antibodies

To characterize the ability of anti-ADDL antibodies to bind and to dissociate immobilized human FcRn, the seven anti-ADDL antibodies herein were evaluated in a Biacore FcRn binding assay, a surrogate system used to evaluate antibody PK and predict the terminal half life ($t_{1/2}$) of antibodies in non-human primates.

Briefly, purified human FcRn protein was immobilized onto a Biacore CM5 biosensor chip and PBSP (50 mM NaPO4, 150 mM NaCl and 0.05% (v/v) Surfactant 20) pH 7.3 was used as running buffer. The mAbs were diluted with PBSP pH 6.0 to 100 nM, allowed to bind FcRn for 3 min to reach equilibrium and followed by dissociation in pH 7.3 running buffer. A report point (Stability) was inserted at 5 seconds after the end of mAb binding and the "% bound" was calculated as $RU_{Stability}/RU_{Binding}$ (%). Applicants found that monoclonal antibodies (mAbs) with identical Fc sequences but different Fab domains can bind and dissociate from FcRn with considerable differences (data not shown). Moreover, an apparent correlation between dissociation at neutral pH and in vivo pharmacokinetics was observed, in which mAbs with slow-dissociation fractions (i.e. higher "% bound") tended to exhibit shorter $t_{1/2}$ in vivo. This feature was used as an in vitro screening tool for antibody pharmacokinetics.

A comparison was made of the seven anti-ADDL antibodies herein, along with h3B3, two ADDL preferring antibodies (Comp 1 and 3) and a non-selective (Comp 2: binds all Aβ forms evaluated) comparator in the FcRn binding assay. A sensorgram was generated (FIG. 5) showing the initial binding of the antibody at pH 6.0 and then the dissociation of the antibody at pH 7.3 from 180 seconds. As shown in FIG. 5, there was a noticeable difference between h3B3 and the other antibodies assessed. While h3B3 had a high percent bound to FcRn, the seven anti-ADDL antibodies of the present invention, as well as the two comparator antibodies exhibited considerably lower binding.

Example 6

Characterization of Anti-ADDL Antibody 19.3

Figure 6B:
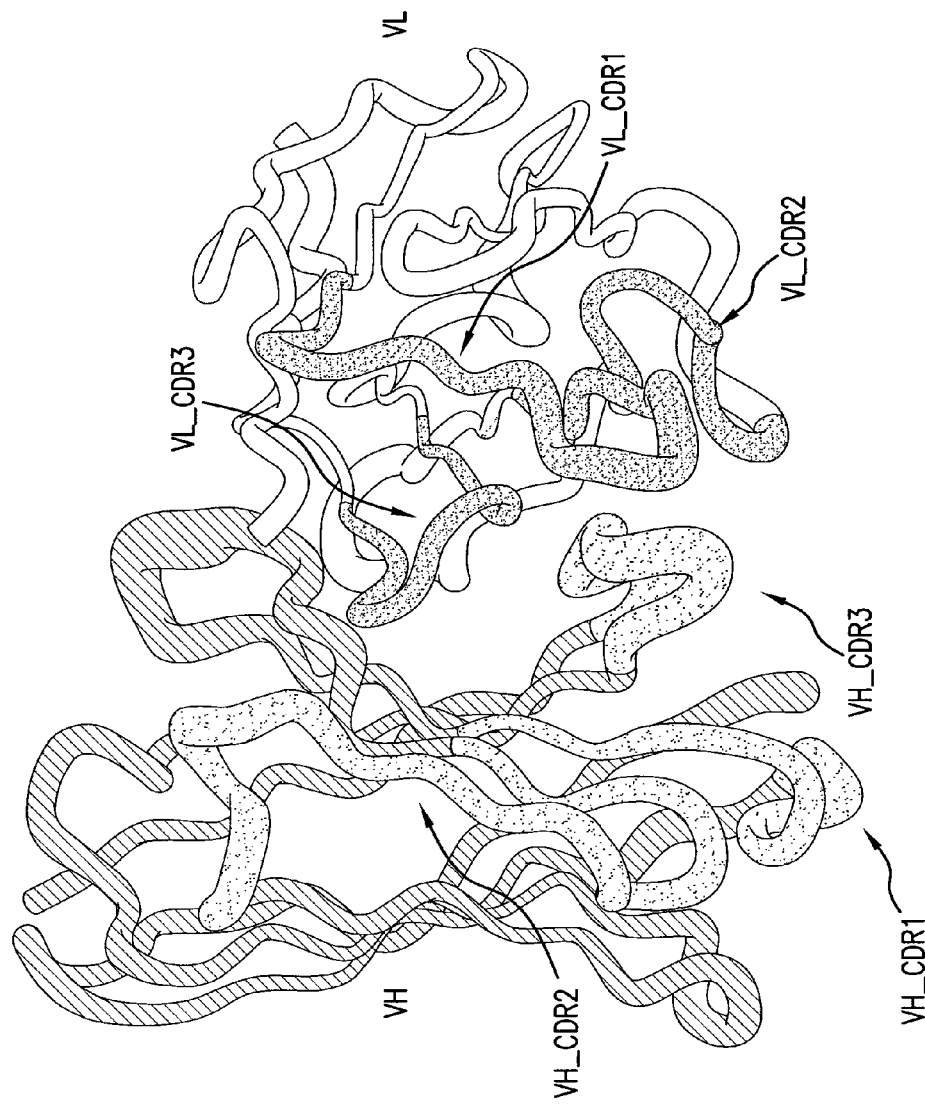
FIG. 6B is a three dimensional model of antibody 19.3 heavy and light variable regions showing the location of the CDRs.

Affinity matured antibody 19.3 was selected for further characterization. The complete DNA sequence and the deduced amino acid sequence for the variable region of the light chain was determined, SEQ ID NOS: 14 and 15, respectively. Alignment of the heavy (SEQ ID NO: 17) and light (SEQ ID NO: 15) chain variable regions is shown in FIG. 6A, together with the closest germ line sequence (SEQ ID NO: 47). A 3D model of heavy and light chain variable regions and the location of the six complementary determining regions (CDRs) are shown in FIG. 6B.

Biacore™ (GE Healthcare, Waukesha, Wis.) and KinExA (Sapidyne, Boise, Id.) analyses were carried out to ascertain the binding affinity of anti-ADDL antibody 19.3 for ADDLs and determine the selectivity of 19.3 for ADDLs versus monomer Aβ. Biacore™ and KinExA based technologies are widely used for the measurement of biding affinity between macromolecules such as antibody and protein target. In the Surface Plasmon Resonance (SPR) technology on which Biacore™ is based, quantitative measurements of the binding interaction between one or more molecules are dependent on the immobilization of a target molecule to the sensor chip surface. Binding partners to the target can be captured as they pass over the chip. Surface Plasmon Resonance (SPR) detects changes in mass in the aqueous layer close to the sensor chip surface by measuring changes in refractive index. When molecules in the test solution bind to a target molecule the mass increases ($k_a$), when they dissociate the mass falls ($k_d$). This simple principle forms the basis of the sensorgram—a continuous, real-time monitoring of the association and dissociation of the interacting molecules. The sensorgram provides quantitative information in real-time on specificity of binding, active concentration of molecule in a sample, kinetics and affinity.

The KinExA technology from Sapidyne Instruments, Boise, Id., measures binding constants to characterize biomolecular binding events in the solution phase, not binding events between a solution phase and a solid phase. In solution, the binding partners reach equilibrium after sufficient incubation. The unbound molecules are quantified with a titration, which will reflect the portion of molecules bound to the partners. The KinExA method does not require modification of molecules under study. With KinExA, the reaction being measured occurs between unmodified molecules in solution. Therefore, concerns of how modification alters "native" binding reactions are eliminated. The KinExA method allows a wider range of binding constants as tight as $10^{-13}$ M. The KinExA software performs data analyses which are based on exact solutions to classic binding equations ($k_d$ mathematics), not pseudo first-order approximations. KinExA does not require arbitrary data manipulations or range selections.

As shown in Table 6, antibody 19.3 had a 4.8 nM affinity for ADDLs as compared to a 150 nM affinity for monomer Aβ in the Biacore™ assay. The thirty fold selectivity of antibody 19.3 for ADDLs over Aβ monomer was markedly better than that seen for the parental antibody, h3B3, which exhibited only a 10 fold preference for ADDLs versus Aβ monomer.

TABLE 6

| Antibody | ADDLs (nM) | Aβ1-40 (nM) | Ratio (Aβ monomer/ADDL) |
|---|---|---|---|
| 3B3 | 10.0 | 104.6 | 10 |
| 19.3 | 4.8 | 150.0 | 31 |

Similarly, antibody 19.3 was evaluated in a KinExA based equilibrium constant measurement. As shown in Table 7, antibody 19.3 had an equilibrium constant of 2.7 nM, which represents more than a six fold preference for ADDL oligomers versus A1340 monomer binding in the same assay.

TABLE 7

| Antibody | ADDLs (nM) | Aβ1-40 (nM) | Ratio (Aβ monomer/ADDL) |
|---|---|---|---|
| 3B3 | 3.3 | 45.0 | 13.6 |
| 19.3 | 2.7 | 16.7 | 6.2 |

Example 7

Biophysical Characterization of Anti-ADDL Antibody 19.3

Biophysical characterization to assess the potential for antibody aggregate formation was carrier out to show that the anti-ADDL antibodies herein are stable under stressed conditions and suitable for use as a therapeutic. Anti-ADDL antibody 19.3 was concentrated to >50 mg/mL and placed in a number of formulations with a pH ranging from 5.0 to 8.0. Two sets of samples were incubated at 37° C. and 45° C. for one week. A third set of samples was placed at −70° C. to initiate a series of five freeze/thaw cycles. Size exclusion chromatography analysis indicated that the antibody preparations were predominantly (>95%) in the monomer state, with small amount of dimers, which were typical for monoclonal antibody preparations. The amount of dimers and higher molecular weight oligomers did not increase after the temperature stress across all buffers and no fragmentation was observed. As summarized in Table 8, the near ultraviolet turbidity analysis also indicated lack of aggregation. The freeze/thaw stressed samples showed buffer-dependent increase in turbidity, which was comparable to other monoclonal antibodies. Viscosity at 50 mg/mL was below 2 centipoise, indicating an acceptable injection viscosity, as the 20 centipoise level is generally considered to be a practical limit for subcutaneous injections. Differential scanning calorimetry also revealed acceptable thermal stability, with Fab unfolding at about 72° C. and the least stable CH2 domain unfolding above 65° C. Taken together, antibody 19.3 demonstrated very good structural stability with biophysical properties compatible with subcutaneous delivery.

TABLE 8

| Antibody | Initial Aggregates (%) | Initial Fragments (%) |
|---|---|---|
| 19.3 | 2.2 | 0.0 |
| Control 1 | 1.6 | 0.4 |
| Control 2 | 2.6 | 0.0 |

Example 8

Pharmacokinetic Analysis of 19.3 and Efficacy in a Model of AD

A. Pharmacokinetics Study in Human FcRn Mice

Human FcRn mice (heterozygous Tg276) (Jackson Laboratories, Bar Harbor, Me.) have recently been suggested as a valuable surrogate system for evaluating monoclonal antibody pharmacokinetics. To characterize the pharmacokinetics of the anti-ADDL antibody 19.3 in human FcRn mice, three animals received a single intravenous injection of antibody 19.3 at 10 mg/kg via tail vein. A series of 10 μL of blood samples were then collected at time points 0, 25, 50, 75, 100, 150, 250 and 350 hours after IV administration of antibody 19.3 or h3B3 and a validated anti-human IgG immunoassay was used to determine blood levels of antibody. As shown in FIG. 7, blood levels for antibody 19.3 declined in a biphasic manner with an apparent $t_{1/2}$ 77±6 hours, which was considerably longer than the half life for the parental antibody, h3B3, of about 29±9 hours. These half lives were in agreement with the difference predicted by the in vitro FcRn binding assay (FIG. 5). The elimination phase terminal half life was determined using non-compartmental model (WinNonlin®, Pharsight, Sunnyvale, Calif.) and data points between day 3 and day 15 post dose.

B. Pharmacokinetics Study in Non-Human Primates

To confirm the predicted $t_{1/2}$ of 19.3 in primates, a primate pharmacokinetics study was conducted for anti-ADDL antibody 19.3 in a cohort of cisterna magna ported rhesus monkeys. Six animals (three male/three female) were dosed with a single intravenous bolus or subcutaneous injection of antibody 19.3 (5 mg/kg) and blood samples collected after antibody administration. Concurrently, CSF samples were collected from the cisterna magna port at 0, 2, 4, 8, 12, 24, 30, 48, 54 and 72 hours and the concentration of antibody 19.3 in the serum and CSF was determined with an anti-human IgG ELISA assay. When the animals were administered a single IV bolus injection of antibody 19.3, a $t_{1/2}$ of 254±28 hours was observed, while a $t_{1/2}$ of 204±49 hours was seen after subcutaneous administration (FIG. 8). In addition, Applicants found that antibody 19.3 was able to cross into the primate CSF, where it increased in concentration during the first 48 hours and peaked at about 0.1% of the antibody dosed (FIG. 9).

C. Distribution of $^{125}$I-Labeled Anti-ADDL Antibody 19.3 in Mouse Brain

In an attempt to determine the concentration of antibody that reached the brain, twelve-month-old male Tg2576 mice (line B6; SJL-TgN APPSWE) were injected (tail vein) with 200 μg of $^{125}$I-labeled 19.3 antibody (~8 mg/kg), or one of two comparator antibodies, and the blood and CSF collected two hours later. The residual radioactivity was cleared from the vessels of the brain via cardiac perfusion with PBS prior to the removal of the brain. A sample of blood, CSF and the whole brain was then placed in a gamma counter to determine the amount of radiolabeled antibody present in each sample. After counting, the brains were fixed in 4% paraformaldehyde for 48 hours and then processed for free-floating immunocytochemistry. The localization of antibody 19.3 in the mouse brain was detected with an anti-human secondary antibody and a standard ABC detection method. This immunoreactivity was then combined with thioflavin S staining (a stain that detects plaques) to determine the colocalization of antibody with plaques in the mouse brain.

Figure 10C:
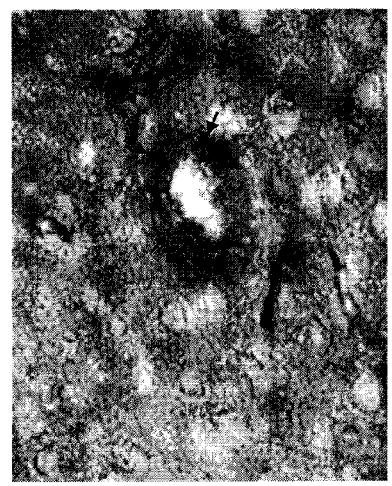

As shown in FIGS. 10A and 10B radiolabeled antibody 19.3 was able to penetrate the blood-brain-barrier into the mouse CSF and brain. Moreover, the data indicated that antibody 19.3 was enriched in the brain (0.19%) when compared with levels seen in the CSF (0.02%). To determine if this concentration in the brain was due to the association of antibody 19.3 with Aβ, the brains were fixed and processed for immunocytochemistry. Analysis of antibody distribution in the aged Tg2576 mouse brain revealed that antibody 19.3 was associated with thioflavin S positive amyloid plaques in the brain (FIGS. 10C and 10D). These data provided the first evidence that antibody 19.3 was able to penetrate into the transgenic mouse brain and bind to Aβ species of interest.

Example 9

Plaque Deposition Model

To further assess the ability of anti-ADDL antibody 19.3 to abate ADDL deposition into amyloid plaques in the brain, twelve-month-old male Tg2576 mice (Taconic, NY) were unilaterally cannulated weekly and bADDLs (50 pmol/μL) infused weekly for four weeks into the hippocampus (FIG. 11A). One week after the last bADDL treatment, half of the mice (n=5/treatment) were dosed (tail vein) weekly, for four weeks with PBS, while the remaining animals were dosed weekly with 200 μg of anti-ADDL antibody (about 8 mg/kg). All animals were euthanized one week after the last treatment and their brains processed for immuno-cytochemistry. For the detection of bADDL and plaques, brain sections were incubated with Streptavidin Alexa Fluor® 594 (Invitrogen, Carlsbad, Calif.), mounted onto slides and the plaques stained with thioflavin S. Fluorescent images of the plaques were then captured with a PerkinElmer Rapid Confocal Imager with UltraVIEW ERS software and the difference in plaque growth quantified. The details of this model were recently published (Gaspar et. al., 2010, *Exp. Neurol.*, 223: 394-400). After one month of treatment, a significant reduction in the deposition of new ADDLs into existing plaques was seen in animals treated with antibody 19.3 (FIG. 11C), when compared to animals treated with vehicle alone (FIG. 11B).

What is claimed:

1. An isolated antibody, or an antigen binding fragment thereof, that binds amyloid β-derived diffusible ligands, said antibody or fragment comprising:
   (a) a light chain variable region comprising,
      (i) a CDR1 of SEQ ID NO:1,
      (ii) a CDR2 of SEQ ID NO:2,
      (iii) a CDR3 of SEQ ID NO:10; and
   (b) a heavy chain variable region comprising,
      (i) a CDR1 of SEQ ID NO:4,
      (ii) a CDR2 of SEQ ID NO:5, and
      (iii) a CDR3 of SEQ ID NO:6.

2. The isolated antibody of claim 1 wherein the light chain variable region of said antibody comprises SEQ ID NO:15 and the heavy chain variable region of said antibody comprises SEQ ID NO:17.

3. The isolated antibody of claim 1 further comprising a heavy chain constant region of SEQ ID NO:21.

4. The isolated antibody of claim 1, wherein the antibody is a monoclonal antibody.

5. A pharmaceutical composition comprising the antibody or antigen binding fragment of claim 1 in admixture with a pharmaceutically acceptable carrier.

6. A method for attenuating binding of amyloid β-derived diffusible ligands to a neuron comprising contacting the neuron with the antibody or antigen binding fragment of claim 1 so that binding of Aβ-derived diffusible ligands to the neuron is attenuated.

7. A method for inhibiting assembly of amyloid β-derived diffusible ligands comprising contacting a sample containing amyloid β 1-42 peptides with the antibody or antigen binding fragment of claim 1 thereby inhibiting assembly of Aβ-derived diffusible ligands.

8. A method for inhibiting the phosphorylation of tau protein at Ser202/Thr205 comprising contacting a sample containing a tau protein with the antibody or antigen binding fragment of claim 1 thereby inhibiting the phosphorylation of tau protein at Ser202/Thr205.

9. A method for attenuating the symptoms of a disease associated with amyloid β-derived diffusible ligands comprising administering an effective amount of the pharmaceutical composition of claim 5.

10. A kit for detecting amyloid β-derived diffusible ligands comprising the antibody or antigen binding fragment of claim 1.

* * * * *